United States Patent [19]
Burks, Jr. et al.

[11] Patent Number: 5,558,869
[45] Date of Patent: Sep. 24, 1996

[54] MAJOR PEANUT ALLERGEN ARA H II

[75] Inventors: A. Wesley Burks, Jr.; Ricki M. Helm, both of Little Rock, Ark.

[73] Assignee: University of Arkansas, Little Rock, Ark.

[21] Appl. No.: 158,704

[22] Filed: Nov. 29, 1993

Related U.S. Application Data

[63] Continuation-in-part of Ser. No. 998,377, Dec. 30, 1992.

[51] Int. Cl.$^6$ .................................................. C07K 14/415
[52] U.S. Cl. ........................ 424/276.1; 424/810; 530/370; 530/403; 530/868
[58] Field of Search ................................ 424/276.1, 810; 530/370, 868, 403

[56] References Cited

U.S. PATENT DOCUMENTS

| | | | |
|---|---|---|---|
| 3,645,852 | 2/1972 | Axen et al. | 435/181 |
| 3,720,760 | 3/1973 | Bennich et al. | 436/513 |
| 4,535,010 | 8/1985 | Axen et al. | 427/246 |

OTHER PUBLICATIONS

Bårnett et al, "Partial Characterization of an allergenic glycoprotein from peanut (*Arachis hypogaea* L.)" Biochimica et Biophysica Acta 882:97–105, 1986.

Thomas et al "Purification of Membrane Proteins" in Methods in Enzymology vol 182:499–520, 1990.

Phadebas RAST ® Radioimmunoassay, © Pharmacia Diagnostics AB, Uppsala, Sweden 1985, Revised Jan. 1988.

The Journal of Allergy and Clinical Immunology, vol. 89, No. 1, Part 2, Jan. 1992, The American Academy of Allergy and Immunology, Abstract 613, Monoclonal Antibody Enzyme–Linked Immunosorbent Assay (Elisa) For Arah I, A Major Peanut Allergen. *G. Cockrell BS, C. Connaughton BS, RM Helm, PHD, A. W. Burks, MD*, Little Rock, Arkansas.

Pharmacia IgE RIA Ultra, © Pharmacia Diagnostics AB, Uppsala, Sweden 1985, Revised May 1988.

Identification, quantitation, and purification of cockroach allergens using monoclonal antibodies; Susan M. Pollart, MD, et al.; J. Allergy Clin Immunol 1991; 87:511–21.

Immunoassay of peanut allergens in food–processing materials and finished foods, *M. U. Keating, MD, et al*; J. Allergy Clin Immunol 1990; 86:41–4.

Monoclonal Antibodies as Structural Probes for Mite, Cat, and Cockroach Allergens; *Martin D. Chapman*; Advances in the Biosciences, vol. 74, © 1989 Pergamon Press plc.

Identification of a major peanut allergen, Ara h I, in patients with atopic dermatitis and positive peanut challenges; *A. Wesley Burks, et al.*, Reprinted from The Journal Of Allergy And And Clinical Immunology, St. Louis, vol. 88, No. 2, pp. 172–179, Aug. 1991, © 1991, by Mosby–Year Book, Inc.

Identification and characterization of a second major peanut allergen, Ara h II, with use of the sera of patients with atopic dermatitis and positive peanut challenge, *A. Wesley Burks, MD, et al.*, Reprinted from The Journal Of Allergy And Clinical Immunology, St. Louis, vol. 90, No. 6, pp. 962–969, Dec., 1992, © 1992, by Mosby–Year Book, Inc.

Voller et al., "Enzyme–Linked Immunosorbent Assay" Chapter 17 in N. R. Rose ed. Manual of Clinical Laboratory Immunology 1986, ASN, pp. 99–109.

Supplement to The Journal of Allergy and Clinical Immunology, vol. 87, No. 1, Part 2, Jan. 1991, The American Academy of Allergy and Immunology, Abstract 209, Isolation Of Peanut Allergens Using Monoclonal Antibodies. *S. L. Hefle, M.S., J. P. Folgert, B.S., F.S., Chu, PhD, R. K. Bush, M.D.*, Madison, WI.

Supplement to The Journal of Allergy and Clinical Immunology, vol. 87, No. 1, Part 2, Jan. 1991, The American Academy of Allergy and Immunology, Abstract 210, Production Of Murine Monoclonal (mAB) Antibodies et Ara h I, A 63.5 kD Allergen In Peanuts., *A. W. Burks, MD, L. W. Williams, MD, R. M. Helm PhD*, Little Rock, Arkansas.

Supplement to The Journal of Allergy and Clinical Immunology, vol. 87, No. 1, Part 2, Jan. 1991, The American Academy of Allergy and Immunology, Abstract 211, Identification Of A Second Major Peanut Allergen In Patients With Atopic Dermatitis And Peanut Hypersensitivy. *A. W. Burks, MD, R. M. Helm PhD, L. W. Williams MD, T. O'Brien PhD*, Little Rock, Arkansas.

*Primary Examiner*—Hazel F. Sidberry
*Assistant Examiner*—Julie Krsek-Staples
*Attorney, Agent, or Firm*—Daniel R. Alexander; Head, Johnson & Kachigian

[57] ABSTRACT

Peanut allergen Ara h II was identified using the sera of patients who had atopic dermatitis and a positive food challenge to peanut. The Ara h II allergen, having a molecular weight of 17 kD and a pI of 5.2, was isolated by anion exchange chromatography. Ara h II may be used to detect and quantify peanut allergens in foodstuffs.

5 Claims, 10 Drawing Sheets

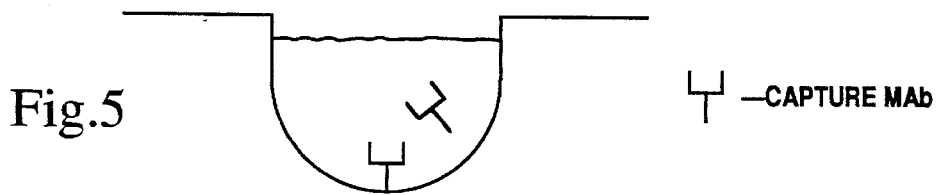
Fig.5  ⊣ —CAPTURE MAb
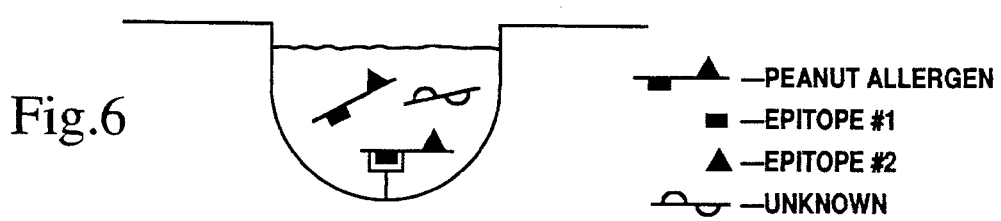
Fig.6
- ■▲ —PEANUT ALLERGEN
- ■ —EPITOPE #1
- ▲ —EPITOPE #2
- ⌒ —UNKNOWN
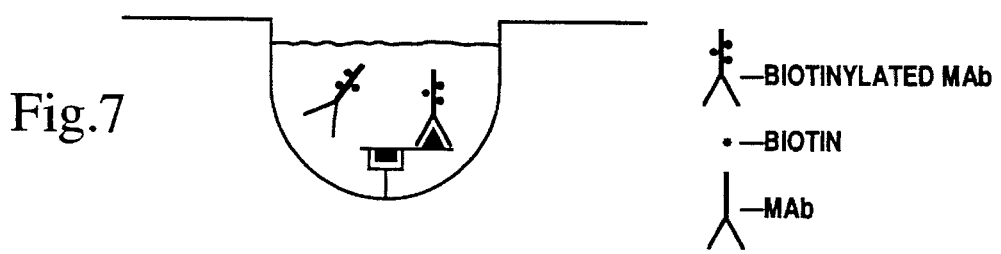
Fig.7
- —BIOTINYLATED MAb
- • —BIOTIN
- ⋏ —MAb
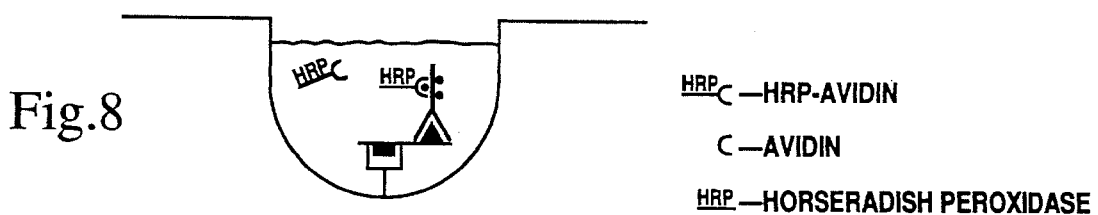
Fig.8
- HRP⊂ —HRP-AVIDIN
- ⊂ —AVIDIN
- HRP —HORSERADISH PEROXIDASE
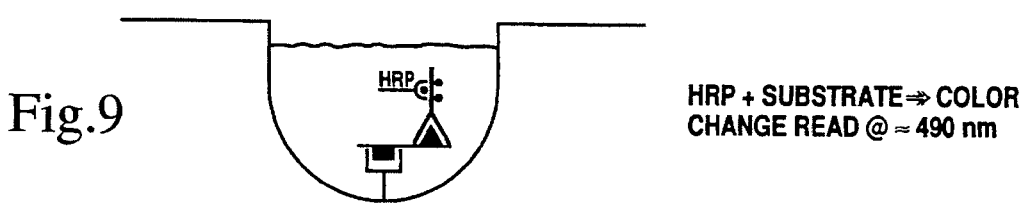
Fig.9  HRP + SUBSTRATE ⇒ COLOR CHANGE READ @ ≈ 490 nm (−)    (+) MW 1
2

3

4

5

6

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 32 amino acid residues
        ( B ) TYPE: Amino acid sequence
        ( C ) STRANDEDNESS: Not Applicable
        ( D ) TOPOLOGY: Unknown to Applicant ( i i ) MOLECULE TYPE: Glycoprotein
        ( A ) DESCRIPTION: 32 N-terminal amino acid residue sequence
            of a 17 kD protein/allergen (upper band)
            isolated from a crude extract of peanuts
            ( A r a c h i s   h y p o g a e a   L . ) identified as Ara h II
            ( I U I S / W H O   n o m e n c l a t u r e )

( i i i ) HYPOTHETICAL: No ( i v ) ANTI-SENSE: Not applicable ( v ) FRAGMENT TYPE: N-terminal fragment ( v i ) ORIGINAL SOURCE:
        ( A ) ORGANISM: Arachis hypogaea L.
        ( B ) STRAIN: Southeastern runners
        ( C ) INDIVIDUAL ISOLATE: Commercial lots North Carolina
            State Univ.
        ( D ) DEVELOPMENTAL STAGE: Mature raw peanuts
        ( E ) HAPLOTYPE: Not applicable
        ( F ) TISSUE TYPE: Mature peanuts
        ( G ) CELL TYPE: Not applicable
        ( H ) CELL LINE: Not applicable
        ( I ) ORGANELLE: Not applicable ( v i i ) IMMEDIATE SOURCE: Crude soluble whole peanut extract
        ( A ) LIBRARY: Not applicable
        ( B ) CLONE: Not applicable ( v i i i ) POSITION IN GENOME: Not applicable ( i x ) FEATURE:
        ( A ) NAME/KEY:
        ( B ) LOCATION: Not registered
        ( C ) IDENTIFICATION METHOD: Not completed
        ( D ) OTHER INFORMATION: Ara h II allergen isolated from
            crude extract of Arachis hypogaea L with an apparent
            molecular wt of 17 kD that binds to IgE in human serum
            from patients with peanut immediate hypersensitivity ( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:

(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO: 1:

| Xaa | Gln | Gln | Xaa | Glu | Leu | Gln | Xaa | Asp | Xaa | Xaa | Xaa |
| 1   |     |     |     | 5   |     |     |     |     | 10  |     |     |

| Gln | Ser | Gln | Leu | Glu | Arg | Ala | Asp | Leu | Arg | Pro | Gly |
|     |     | 15  |     |     |     |     | 20  |     |     |     |     |

| Glu | Gln | Xaa | Leu | Met | Xaa | Lys | Ile |
| 25  |     |     |     |     | 30  |     |     |

(2) INFORMATION FOR SEQ ID NO: 2:

(i) SEQUENCE CHARACTERISTICS:
(A) LENGTH: 32 amino acid residues
(B) TYPE: Amino acid sequence
(C) STRANDEDNESS: Not Applicable
(D) TOPOLOGY: Unknown to Applicant (ii) MOLECULE TYPE: Glycoprotein
(A) DESCRIPTION: 32 N-terminal amino acid residue sequence
of a 17 kD protein/allergen (lower band)
isolated from a crude extract of peanuts
(Arachis hypogaea L.) identified as Ara h II
(IUIS/WHO nomenclature)

(iii) HYPOTHETICAL: No (iv) ANTI-SENSE: Not applicable (v) FRAGMENT TYPE: N-terminal fragment (vi) ORIGINAL SOURCE:
(A) ORGANISM: Arachis hypogaea L.
(B) STRAIN: Southeastern runners
(C) INDIVIDUAL ISOLATE: Commercial lots North Carolina
State Univ.
(D) DEVELOPMENTAL STAGE: Mature raw peanuts
(E) HAPLOTYPE: Not applicable
(F) TISSUE TYPE: Mature peanuts
(G) CELL TYPE: Not applicable
(H) CELL LINE: Not applicable
(I) ORGANELLE: Not applicable (vii) IMMEDIATE SOURCE: Crude soluble whole peanut extract
(A) LIBRARY: Not applicable
(B) CLONE: Not applicable (viii) POSITION IN GENOME: Not applicable (ix) FEATURE:
(A) NAME/KEY:
(B) LOCATION: Not registered
(C) IDENTIFICATION METHOD: Not completed
(D) OTHER INFORMATION: Ara h II allergen isolated from
crude extract of Arachis hypogaea L with an apparent
molecular wt of 17 kD that binds to IgE in human serum
from patients with peanut immediate hypersensitivity (x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO: 2:

```
            Xaa    Gln    Gln    Xaa    Glu    Leu    Gln    Asp    Leu    Glu    Xaa    Xaa
            1                           5                                  10

Gln    Ser    Gln    Leu    Glu    Asp    Ala    Asn    Leu    Arg    Pro    Arg
                          15                                 20

Glu    Gln    Xaa    Leu    Met    Xaa    Lys    Ile
            25                          30
```

( 2 ) INFORMATION FOR SEQ ID NO: 3:

( i ) SEQUENCE CHARACTERISTICS:
        ( A ) LENGTH: 9 amino acid residues
        ( B ) TYPE: Amino acid sequence
        ( C ) STRANDEDNESS: Not Applicable
        ( D ) TOPOLOGY: Unknown to Applicant ( i i ) MOLECULE TYPE: Glycoprotein
        ( A ) DESCRIPTION: 9 N-terminal amino acid residue sequence
            of a 17 kD protein/allergen (lower band)
            isolated from a crude extract of peanuts
            ( A r a c h i s   h y p o g a e a   L . ) identified as Ara h II
            ( I U I S / W H O   n o m e n c l a t u r e )

( i i i ) HYPOTHETICAL: No ( i v ) ANTI-SENSE: Not applicable ( v ) FRAGMENT TYPE: N-terminal fragment ( v i ) ORIGINAL SOURCE:
        ( A ) ORGANISM: Arachis hypogaea L.
        ( B ) STRAIN: Southeastern runners
        ( C ) INDIVIDUAL ISOLATE: Commercial lots North Carolina
            State Univ.
        ( D ) DEVELOPMENTAL STAGE: Mature raw peanuts
        ( E ) HAPLOTYPE: Not applicable
        ( F ) TISSUE TYPE: Mature peanuts
        ( G ) CELL TYPE: Not applicable
        ( H ) CELL LINE: Not applicable
        ( I ) ORGANELLE: Not applicable ( v i i ) IMMEDIATE SOURCE: Crude soluble whole peanut extract
        ( A ) LIBRARY: Not applicable
        ( B ) CLONE: Not applicable ( v i i i ) POSITION IN GENOME: Not applicable ( i x ) FEATURE:
        ( A ) NAME/KEY:
        ( B ) LOCATION: Not registered
        ( C ) IDENTIFICATION METHOD: Not completed
        ( D ) OTHER INFORMATION: Ara h II allergen isolated from
            crude extract of Arachis hypogaea L with an apparent
            molecular wt of 17 kD that binds to IgE in human serum
            from patients with peanut immediate hypersensitivity ( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO: 3:

```
            Xaa    Gln    Gln    Xaa    Glu    Leu    Gln    Asp    Leu
            1                           5
```

MAJOR PEANUT ALLERGEN ARA H II

CROSS-REFERENCE TO RELATED APPLICATIONS

This application is a continuation-in-part of copending application Ser. No. 07/998,377 filed Dec. 30, 1992.

BACKGROUND OF THE INVENTION

The present invention is directed to methods and apparatus for detecting and quantifying allergens in foodstuffs, and, more particularly, concerns peanut allergens, antigens, monoclonal antibodies having specificity for peanut allergens, hybridoma cell lines which produce the monoclonal antibodies and immunoassay methods and apparatus including the monoclonal antibodies for detecting and quantifying peanut allergens in food-processing equipment and materials as well as natural, processed, and finished foods.

The ingestion of peanuts is a common cause of food hypersensitivity reactions. Symptoms can vary from mild abdominal discomfort to severe anaphylaxis. In a recent report by Yunginger et al., "Fatal Food-Induced Anaphylaxis", *Journal of the American Medical Association* 1988; 260:1450–2, four of seven patients who experienced fatal anaphylaxis died after peanut ingestion. All four of these patients unknowingly had eaten peanut in food prepared and consumed away from home. In the most recent studies involving children and food challenges, peanut is among the three leading foods that cause food hypersensitivity reactions.

The increasing use of peanut products in our food supply has served to aggravate the problem of peanut allergy. Peanuts, generally in the form of peanut butter, are introduced into the American diet at a very young age. Some children react on challenge to peanut on their first known exposure, indicating that they had been sensitized in utero, by breast feeding, or by an unknown exposure. Unlike other food sensitivities in children, long-term follow-up studies of up to fourteen years indicate that peanut hypersensitivity is rarely outgrown.

It is important for peanut-sensitive individuals to have a means of recognizing and avoiding peanut-containing products. Unfortunately, peanut allergens have been identified in non-peanut foodstuffs manufactured on common processing equipment that were inadequately cleaned. Peanut products that serve as substitutes for other nuts in candles are not uncommon. In patients suffering from extrinsic asthma, hayfever, or atopic eczema, symptoms develop immediately after exposure to specific allergens. This immediate type of allergy is a function of a special type of serum antibodies called reagins. These reagins have been identified as belonging to the IgE class of immunoglobulins. Radioimmunoassays (RIA) have been developed to measure the level of circulating allergen specific IgE in human blood samples.

For example, Pharmacia Diagnostics AB, Uppsala, Sweden, manufactures a Phadebas RAST® radioimmunoassay (U.S. Pat. Nos. 3,645,852 and 3,720,760). The Phadebas Rast® radioimmunoassay is an in vitro test system based on the Radio Allegro Sorbent Test principle for determination of circulating specific IgE antibodies. The allergen of interest is covalently coupled to a solid phase. The allergen is reacted with a patient serum sample containing both allergen specific and non-specific IgE. The allergen reacts with the specific IgE in the patient sample. After washing away non-specific IgE, radioactively labeled antibodies against IgE are added forming a complex. Then unbound radioactively labeled anti-IgE is washed away. Next, the radioactivity of the bound complex is measured in a gamma counter. The more bound radioactivity found, the more specific IgE present in the sample. To classify the test results, patient counts are compared directly with counts of reference sera run in parallel. This system is designed for use in testing allergens including grass, tree, weed pollens, house dust, mites, foods, insects, epidermals, molds, drugs, occupational allergens, and parasites.

Pharmacia Diagnostics AB, Uppsala, Sweden also manufactures a Pharmacia IgE RIA Ultra solid-phase, sandwich radioimmunoassay for quantitative determination of total IgE in human serum. The serum concentration of IgE is significantly elevated in most patients with allergic diseases, such as extrinsic asthma, hayfever, and atopic disease. In this system, a monoclonal anti-IgE is covalently coupled to a test tube wall. This monoclonal reacts with the IgE in the samples during a first incubation. The tubes are then washed and radioactively labeled anti-IgE reacts with the bound IgE during a second incubation. After the second incubation, unbound radioactively labeled anti-IgE is washed away. The radioactivity in the tube is then measured and is directly proportional to the concentration of the IgE in the sample.

The use of a radioimmunoassay to detect peanut allergens in food processing materials and finished foods is described in a Keating et al. article entitled "Immunoassay of Peanut Allergens in Food Processing Materials and Finished Foods", appearing in the *Journal of Allergy Clinical Immunology* 1990; 86:41–4. To quantitate trace amounts of peanut allergens in food processing materials and finished foods, there was established a solid-phase radioimmunoassay inhibition using pooled sera from five peanut-sensitive subjects and roasted peanut meal extract covalently linked to polyacrylamide beads. Test samples were extracted, dialyzed, lyophilized, and reconstituted at 10 to 125 mg of dry weight per ml concentrations. The peanut allergen content of test samples was expressed relative to a reference extract of roasted peanut meal that was assigned an arbitrary potency of 100,000 U/ml. In confectionary products spiked with varying quantities of peanut, the recovery of peanut allergen ranged from 31% to 94%. The sensitivity of the assay was 2.5 U/mg of dry weight from the samples. Peanut allergens were undetectable in virgin vegetable oil used to roast peanuts, but 600 to 760 U/mg of dry weight were present in oil after varying periods of use. The allergen content of used oil was reduced to 8 U/mg of dry weight by filtration and steam cleaning. The availability of such a radioimmunoassay provides a way of monitoring finished food products for potential allergens.

In light of the foregoing, there is a need for an improved immunoassay for detecting and quantifying specific peanut allergens in food processing materials, equipment, and raw, processed, and finished foods.

SUMMARY OF THE INVENTION

In accordance with the present invention, specific peanut allergens are identified and a monoclonal antibody based assay is provided for detecting and quantifying the specific peanut allergens.

The identification of a major peanut allergen, Ara h I, is described in an article "Identification of a Major Peanut Allergen In Patients With Atopic Dermatitis and Positive Peanut Challenges" by Burke et al., *The Journal of Clinical Immunology*, August 1991; Vol. 88, No. 2, pp 122–179. Serum from nine patients with atopic dermatitis in a positive double-blind, placebo-controlled food challenge to peanut was used to begin the process of identification and purification of the major peanut allergens. Identification of a major peanut allergen was accomplished by use of anion-exchange column chromatography, sodium dodecyl sulphate-polyacrylamide gel electrophoresis, ELISA, thin layer isoelectric focusing, and IgE-specific immunoblotting. Anion-exchange chromatography revealed several fractions that bound IgE from the serum of the challenged positive patient pool. By measuring anti-peanut-specific IgE in the ELISA and IgE-specific immunoblotting, there was identified an allergenic component with two Coomassie brilliant blue staining bands by sodium dodecyl sulphate-polyacrylamide gel electrophoresis with a mean molecular weight of 63.5 kD. Examination of this fraction by the IgE anti-peanut ELISA with individual serum and by the ELISA-inhibition assay with pooled serum, lead to its identification as a major allergen. Thin layer isoelectric focusing and immunoblotting of the 63.5 kD fraction revealed it to have an isoelectric point (pI) of 4.55. Based on allergen nomenclature of the IUIS subcommittee for allergen nomenclature, this allergen was designated Ara h I (*Arachis hypogaea*), Burks et al. also identified and characterized a second major peanut allergen, Ara h II, as described in an article entitled "Identification and Characterization of A Second Major Peanut Allergen, Ara h II, With Use of the Sera of Patients with Atopic Dermatitis in Positive Peanut Challenge", *Journal of Allergy and Clinical Immunology*, December 1992; Vol. 90. Again, serum from nine patients with atopic dermatitis in a positive double-blind, placebo controlled, food challenge to peanut was used in the process of identification and purification of the peanut allergen. Identification of a second major peanut allergen was accomplished with the use of various biochemical and molecular techniques, Anion exchange chromatography of the crude peanut extract produced several fractions that bound IgE from the serum of the patient pool with positive challenges. By measuring anti-peanut specific IgE and by IgE specific immunoblotting, there was identified an allergic component that has two closely migrating bands with a mean molecular weight of 17 kD. Two-dimensional gel electrophoresis of this fraction revealed it to have a mean isoelectric point of 5.2. According to allergen nomenclature of the IUIS subcommittee for allergen nomenclature, this allergen is designated, Ara h II (*Arachis hypogaea*).

The Ara h I allergen bound IgE in over 90% of a group of six patients with peanut hypersensitivity as shown in Table 1. Multiple monoclonal antibodies were made to this peanut allergen as shown in Table 2. Two of these monoclonal antibodies recognizing distinct epitopes were chosen to prepare a two-site immunometric ELISA for quantitating the 63.5 kD peanut allergen in food products. One was chosen as the capture monoclonal antibody and the other was biotinylated and used as the detection monoclonal antibody in an avidin-biotin assay.

In accordance with one embodiment of the present invention, defatted roasted Florunner peanuts were used as the peanut standard. A microtiter plate was coated with 1 µg/ml of the capture monoclonal antibody 8F10. After incubation for one hour, the plate was washed three times and either the peanut standard or an unknown sample was added. The Florunner standard extract ranged from 0.01 ng/ml to 10 ng/ml total protein. Following incubation at 25° C. for one hour, the plates were washed and then the biotinylated second antibody 8D9 was added at a concentration of 1:500 v/v. The plates were again incubated at 25° C. for one hour and developed by the addition of a horseradish peroxidase-avidin (HRP-avidin) conjugate, followed by citric acid substrate and stopped by the addition of 2N hydrochloric acid. The microtiter plates were read at 495 nm on a Titertek Multiscan. The results were plotted on a log-logit paper to obtain 63.5 kD allergen concentration from the standard curve (see FIG. 1). The assay had an inter-assay coefficient of variation of less than 6%. In each sample run, the linear correlation coefficient was greater than or equal to 0.98.

As shown in Table 3, test samples Included commercially purchased candies and oils. Candies that included peanut on the label and other candies that did not have peanut as a listed ingredient were tested. Also, oils made from either peanut or vegetable oils were tested. Samples were prepared by weighing out 2.5 gms of each candy and then extracting each in 50 ml of 1 M NaCl, 20 mM $NaH_2PO_4$ and 8 M urea with constant agitation overnight at 4° C. Particulate material was removed by filtration through 4×4 rayon polyester gauze (Johnson & Johnson). The sample was then centrifuged at 18,000 rpm for one hour and the supernatant collected. After dialysis, all fractions were lyophilized and stored at 4° C. until used in the assay.

Table 4 shows the results of the monoclonal antibody ELISA with the different candy products. The first column shows the results of the candies with peanut listed on the label. The results range from Peanut Butter M&M's® with 299 ng/ml of allergen to plain M&M's® with 7.35 ng/ml of allergen. The second column shows the results of the five candies tested with no peanut listed on the label. No peanut allergen could be detected in any of these candies.

Table 5 shows the results of the monoclonal antibody ELISA for the various oils tested. No Ara h I could be detected in any of the oils tested from peanut, vegetable, canola, or soybean oil. No oil was tested that had previously been used for roasting peanuts. The lower limits of detection of added peanut to a candy product in this assay appears to be approximately 1% peanut.

The ELISA assay of the present invention differs from the radioimmunoassay (RIA) developed by Yunginger et al. in several ways. The Yunginger RIA is an RIA-inhibition assay with pooled human IgE serum from peanut-sensitive patients as the detection antibody. In the RIA-inhibition assay the serum IgE pool from peanut positive individuals would contain IgE antibody against more allergens than just Ara h I. In contrast, the present ELISA assay can be used to determine the concentration of a specific peanut allergen (Ara h I) in extracted peanut products.

With the use of the present monoclonal antibody ELISA, questions regarding threshold exposure levels in highly allergic patients can be answered and can provide a way to correlate quantities of ingested allergens with the development of clinical symptoms. Contamination of products with other food proteins occurs more frequently than probably appreciated. The ability to monitor food products with the potential to be contaminated is important. The present assay provides a new level of sophistication in the study of peanut hypersensitivity.

The principle object of the present invention is the provision of a monoclonal antibody enzyme-linked immunosorbent assay for peanut allergen. Another object of the present invention is the isolation and purification of peanut allergens. A still further object of the present invention is the provision of peanut allergen antigens and monoclonal antibodies having specificity for a selected peanut allergen antigen. Yet another object of the present invention is the provision of hybridomas which produce monoclonal antibodies specific for peanut allergen.

Still yet another object of the present invention is the provision of a two-site monoclonal antibody based enzyme-linked immunosorbent assay that can be used to detect and determine the concentration of a specific peanut allergen such as Ara h I in a food product or food processing and producing equipment or materials.

Another object of the present invention is the provision of a process for producing monoclonal antibodies specific to a selected peanut allergen, hybridoma cell lines which produce such monoclonal antibodies, and an immunoassay which utilizes the monoclonal antibodies for detecting the presence and concentration of a selected peanut allergen. And, still yet another object of the present invention is the provision of a monoclonal antibody based enzyme-linked immunosorbent assay which does not contain human blood derivatives or radioactively labeled antibodies.

Other objects and further scope of the applicability of the present invention will become apparent from the detailed description to follow taken in conjunction with the accompanying drawings wherein like parts are designated by like reference numerals.

BRIEF DESCRIPTION OF THE DRAWINGS

FIGS. 5–9 are schematic Illustrations of a two-site monoclonal antibody enzyme-linked immunosorbent assay In accordance with one embodiment of the present invention;

DETAILED DESCRIPTION OF THE PREFERRED EMBODIMENTS

Figure 1:
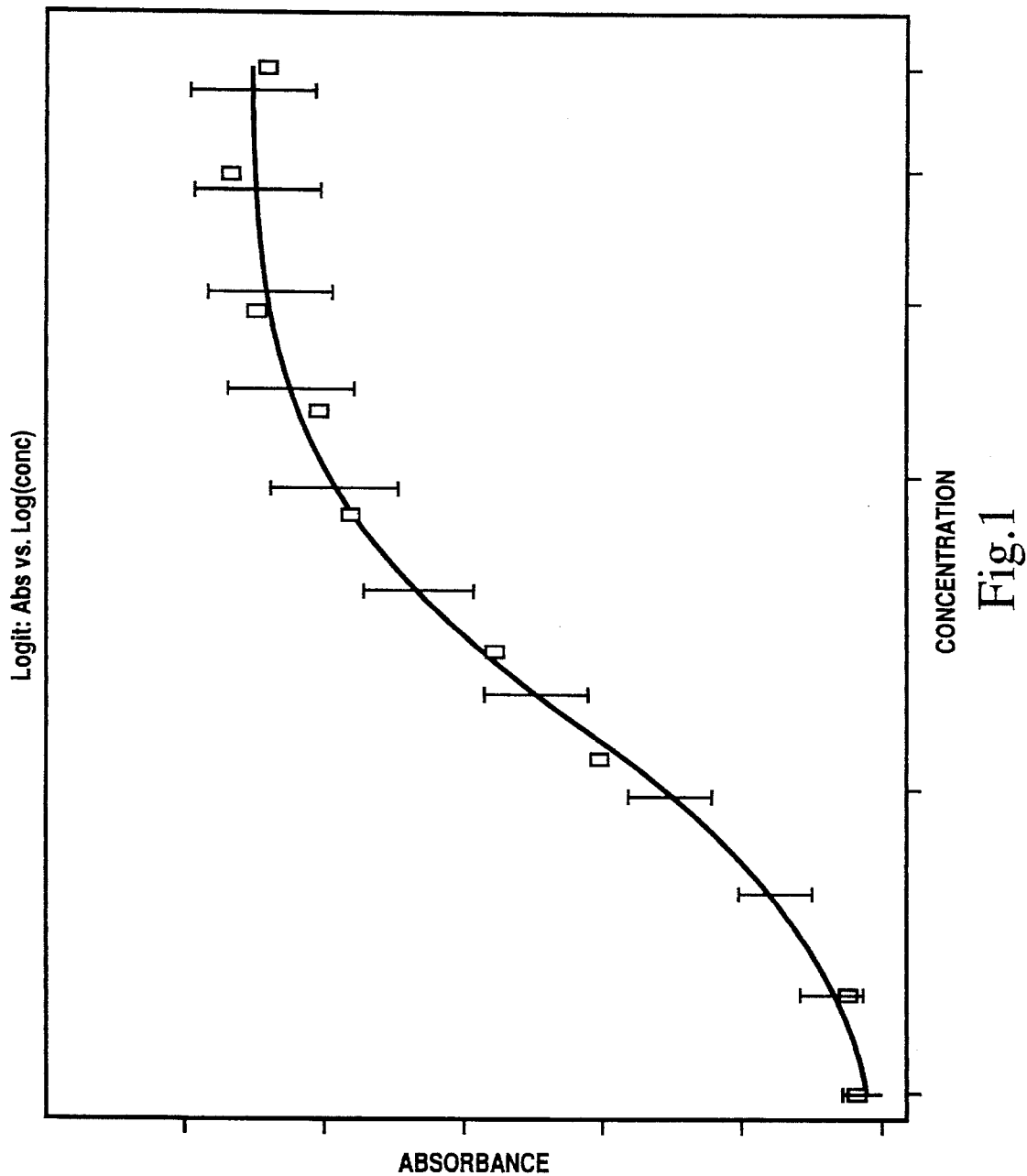
FIG. 1 is a graphical representation of absorbance relative to allergen concentration.

Peanuts are a common cause of food hypersensitivity reactions. The sera of 10 patients who had atopic dermatitis and a positive double-blind placebo-controlled food challenge to peanut were used to investigate the major allergens of peanut. Crude Florunner extracts were fractionated by anion-exchange chromatography using a step gradient (limit buffer, 0.05M BisTris/1.5BM NaCl). One hundred microliters of each 2.0 ml fraction was dot-blotted onto nitrocellulose paper and IgE-binding activity assessed using the serum pool to select allergen-containing fractions. A protein peak (OD 280) which eluted at 10% NaCl and demonstrated intense IgE-binding was further analyzed by two-dimensional SDS-PAGE/immunoblot analysis. The majority of this fraction is a protein which has a molecular weight of 17 kD and a pI of 5.2. sequencing data from the N-terminus revealed the following initial 9 amino acids: (*)-Q-Q-(*)-E-L-Q-D-L. Based on IgE-binding activity and no known amino acid sequence identity to other allergens, this allergen is designated Ara h II.

In accordance with a preferred embodiment of the present invention, a monoclonal antibody (MAb) based enzyme-linked immunosorbent assay (ELISA) and method Is provided for detecting and quantifying a major peanut allergen, Ara h I, in food products. The Ara h I peanut allergen (63.5 kD fraction) was used as an immunogen to produce monoclonal antibodies (MAbs) having specificity for the selected peanut allergen. The Ara h I allergen was isolated as described in the Burks et al. article entitled "Identification of a Major Peanut Allergen, Ara h I, in Patients With Atopic Dermatitis and Positive Peanut Challenges", *Journal of Allergy Clinical Immunology* 1991; 88:172–9.

Patients with atopic dermatitis (AD) who had positive double-blind, placebo controlled, food challenge to peanut were used in the process of identification and purification of the peanut allergens. A major peanut allergen, Ara h I, was identified by use of anion-exchange column chromatography, sodium dodecyl sulphate polyacrylamide gel electrophoresis (SDS-PAGE), ELISA, thin layer isoelectric focusing (TLIEF) and IgE-specific immunoblotting. The Ara h I allergen is a glycoprotein from a pure strain of Florunner peanuts that has a mean molecular weight of 63.5 kD and a mean isoelectric point (pI) of 4.55.

Nine patients (mean age 4.2 years) with AD and a positive immediate prick skin test to peanut had either a positive DBPCFC or a convincing history of peanut anaphylaxis. (The allergic reaction was potentially life-threatening, that is, laryngeal edema, severe wheezing and/or hypotension.) Five milliliters of venous blood was obtained from each patient and allowed to clot, and then the serum was collected. An equal volume of serum from each donor was mixed to prepare a nine-person, peanut-specific, IgE antibody (Ab) pool.

Three commercial lots of southeastern runners (*Arachis hypogaea*) (Florunner), medium grade peanuts from the 1979 crop (North Carolina State University), were used In this study. The peanuts were stored in the freezer at −18° C. until they were roasted. The three lots were combined in equal proportions and blended before defatting. The defatting process (defatted with hexane after roasting for 13 to 16 minutes at 163° to 177° C.) was done in the laboratory of Dr. Clyde Young (North Carolina State University). The powdered crude peanut was extracted according to the recommendations of Yunginger (Yunginger J W, Jones R T. A review of peanut chemistry: implications for the standardization of peanut extracts. In *Proceedings of the Fourth International Paul Ehrilich Seminar on the Regulatory Control and Standardization of Allergenic Extracts.* Bethesda, Md., Oct. 16–17, 1985, Stuttgart: Gustav Fischer Verlag, 1987:251–64) in 1 mol/L of NaCl to 20 mmol/L of sodium phosphate (pH 7.0), with the addition of 8 mol/L of urea for 4 hours at 4° C. The extract was isolated by centrifugation at 20,000 g for 60 minutes at 4° C.

Analytic and preparative anion-exchange chromatography was performed with the fast protein liquid chromatography (FPLC) system (Pharmacia, Piscataway, N.J.). Anion-exchange chromatography was used with the Mono Q 5/5 and 10/10 columns (Pharmacia). The crude peanut extract was dialyzed against 20 mmol/L of Tris-bis-propane (pH 7.2) and 8 mol/L of urea, and 40 mg was loaded onto the Mono Q 10/10 column. A stepwise salt gradient of 0 to 1.5 mol/L of NaCl was applied. All fractions of each resolved peak were pooled, dialyzed, and lyophilized.

Dot blotting was done to determine which fractions from the anion-exchange column chromatogram contained IgE-binding material. The collected fractions (200 µl) were blotted with the Mini Blot apparatus (Schleicher & Schuell Inc., Keene, N.H.) onto 0.45 micron nitrocellulose membranes (Bio-Rad Laboratories, Richmond, Calif.). After membranes were dried, the remaining active sites were blocked with 20 ml of blocking solution (0.5% gelatin with 0.001% thimerosol in 500 ml of PBS) for 1 hour. The procedure is then identical to the immunoblotting for IgE described below.

The electrophoresis procedure was a modification of the method of Sutton et al. (Sutton R, Wrigley C W, Baldo B A. Detection of IgE and IgG binding proteins after electrophoresis transfer from polyacrylamide gels. *Journal of Immunological Methods,* 1982; 52:183–6.) SDS-PAGE was performed with a 12.5% polyacrylamide separating gel and a stacking gel of 3%. Twenty microliters of a 1 mg/ml solution of each protein was applied to each well. Replicate samples were applied for independent analysis. Electrophoresis was performed for 4 hours at 0.030 A per gel (E-C Apparatus Corp., St. Petersburg, Fla.) for the 14 cm by 12 cm gels, and for 1 hour at 175 V per gel for the 8 cm by 7.5 cm gels (Mini-Protean II system, Bio-Rad Laboratories). To assure proper protein separation and visualization, Coomassie brilliant blue (Sigma Chemical Co., St. Louis, Mo.) stains were done on the gels. For detection of carbohydrate staining material, gels were stained with the modified PAS stain according to the method of Kapitany (Kapitany R. Zebrowski E J. A high resolution PAS stain for polyacrylamide gel electrophoresis. *Anal Biochem* 1973; 56:361–9).

Proteins were electrophoretically transferred from the separating gel to a nitrocellulose membrane in a transfer buffer (Tris-glycine) with 10% SDS and 40% methanol. The procedure was done in a transblot apparatus (Bio-Rad Laboratories) for 2 hours (0.150 A) (regular size transfer apparatus for crude peanut and minitransfer apparatus for fraction 3). An amido black stain (Bio-Rad Laboratories) was done to assure transfer of the protein.

After removal from the transblot apparatus, the nitrocellulose was placed in blocking solution overnight at 4° C. The nitrocellulose blot was then washed three times with PBS (PBS with 0.05% Tween 20) and incubated with the pooled serum (1:20 vol/vol dilution) for 2 hours at 4° C. with rocking. After the nitrocellulose blot was again washed with PBS three times, alkaline phosphatase-conjugated goat anti-human IgE (1:1000 vol/vol of PBS, Bio-Rad Laboratories) was added and incubated at room temperature with rocking for 2 hours. After an additional wash with PBS three times, the blot was developed with 250 µl of 30 mg of nitro blue tetrazolium in 70% dimethylformamide and 250 µl of 15 mg of 5-bromo-4-chloro-3-indolyl-phosphate in 70% dimethylformamide (Bio-Rad Laboratories) solutions in 25 ml of carbonate buffer (0.2 mol/L, pH 9.8) at room temperature for 15 minutes. The reaction was then stopped by decanting the 30 mg of nitro blue tetrazolium in 70% dimethylformamide/ 15 mg of 5-bromo- 4-chloro-3-indolyl-phosphate in 70% dimethylformamide solution and incubating the nitrocellulose for 10 minutes with distilled water. The blot was then air-dried.

A biotin-avidin ELISA was developed to quantify anti-peanut protein Abs with modifications from an assay previously published. The upper two rows of a 96-well microtiter plate (Gibco, Santa Clara, Calif.) were coated with 100 µl each of equal amounts (1 µg/ml) of antihuman IgE MAbs, 7.12 and 4.15 (kindly provided by Dr. A. Saxon) in coating buffer (0.1 mol/L of sodium carbonate-bicarbonate buffer, pH 9.5). The remainder of the plate was coated with one of the peanut extracts at a concentration of 1 µg/ml in coating buffer. The plate was incubated at 37° C. for 1 hour and then was washed five times with rinse buffer (PBS, pH 7.4, containing 0.05% Tween 20; Sigma Chemical Co.) immediately and between subsequent incubations. In the upper two rows we used a secondary standard IgE reference to generate a curve for IgE, ranging from 0.05 to 25 ng/ml.

The serum pool and individual patient serum samples were diluted (1:20 vol/vol) and dispensed in duplicate in the lower portion of the plate. After incubation for 1 hour at 37° C. and a subsequent washing, biotinylated, affinity-purified, goat antihuman IgE (KPL, Gaithersburg, Md.) (1:1000 vol/vol of PBS) was added to all wells. Plates were incubated again for 1 hour at 37° C. and washed, and 100 µl of horseradish peroxidase-avidin conjugate (Vector Laboratories, Burlingame, Calif.) was added for 30 minutes. After plates were washed, they were developed by the addition of a buffer containing o-phenylenediamine (Sigma Chemical Co.). The reaction was stopped by the addition of 100 µl of 2-N-hydrochloric acid to each well, and absorbance was read at 492 nm (Titertek Multiscan, Flow Laboratories, McLean, Va.). The standard curve was plotted on a log-logit scale by means of simple linear regression, and values for the pool and individual patient samples were read from the curve as "nanogram-equivalent units" per milliliter (nanogram per milliliter).

A competitive ELISA-inhibition analysis was done with the FPLC fractions. One hundred microliters of pooled serum (1:20 vol/vol) from the positive-challenge patients was incubated with various concentrations of the FPLC protein fractions (0.00005 to 50 ng/ml) for 18 hours at 4° C. The inhibited pooled serum was used in the ELISA described above. The percent inhibition was calculated by taking the food-specific IgE value divided by the food-specific IgE value. The number is multiplied by 100 to get the percentage of inhibition.

The samples were focused with the LKB Multiphor system with LKB PAG plates, pH gradient, 3.5 to 6.85 (LKB, Bromma, Sweden). Five microliters of sample (100 µg of protein) was applied, and an electric current of 200 V was applied for 30 minutes. The gel was fixed and stained with Coomassie brilliant blue following the standard protocol (LKB). For IgE immunoblotting, the protein was transferred to nitrocellulose by capillary transfer and stained as described in the immunoblotting section above.

Figure 2:
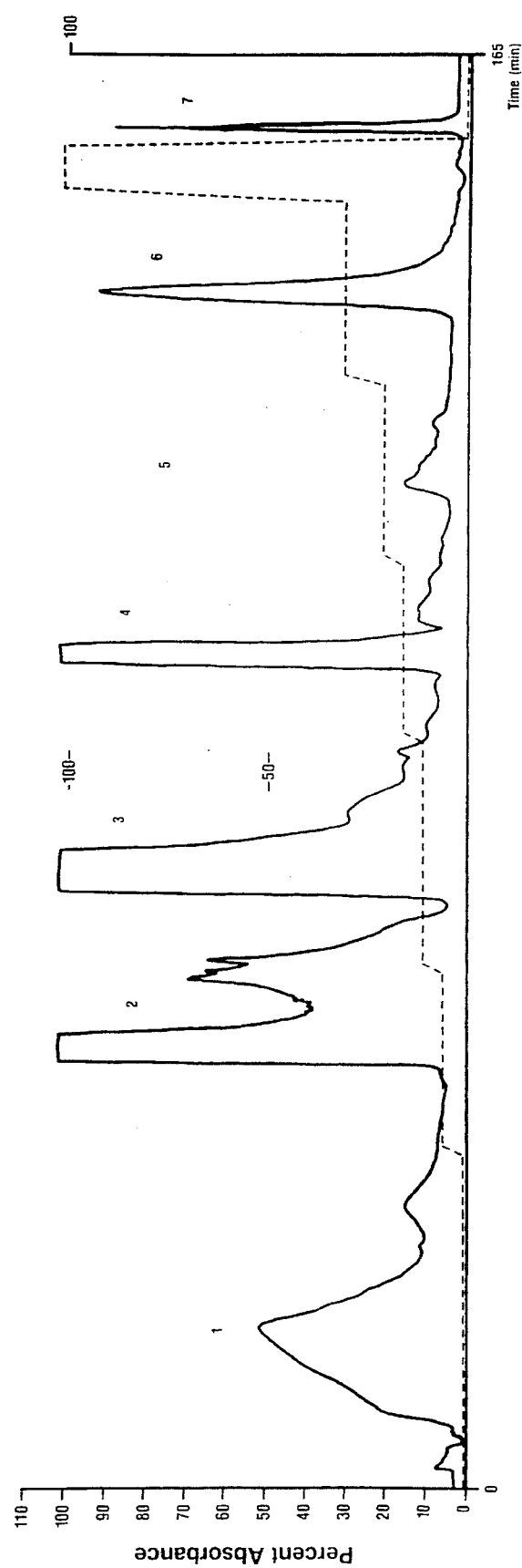
FIG. 2 is an Illustration of the anion-exchange chromatogram of the crude peanut extract.

Pilot experiments were conducted with the analytical Mono Q 5/5 anion-exchange column to determine the optimal buffer system and salt gradient. Scale up and optimization was completed with the Mono Q 10/10, with a stepwise salt gradient (0 to 1.5 mol/L of NaCl). The procedure separated the crude peanut extract into seven peaks (see FIG. 2). Preliminary dot blotting from the separation identified IgE-binding material in each peak. Multiple runs of this fractionation procedure were performed, and each isolated peak was pooled, dialyzed against 100 mmol/L of $NH_4HCO_3$, and lyophilized. Preliminary separation of crude peanut extract with gel filtration (Superose) did not significantly enrich the purification process.

Initial SDS-PAGE and immunoblotting of the crude peanut extract revealed multiple protein fractions with several IgE-staining bands. Aliquots of the seven lyophilized fractions from the anion-exchange column were analyzed by SDS-PAGE. Immunoblotting for specific IgE with the pooled serum revealed two closely migrating bands that bound significant IgE. Preliminary blots with normal control serum and with serum from patients with elevated serum IgE values revealed no non-specific binding to this fraction. The two bands in fraction 3 stained positive for PAS. In addition, this fraction did not bind to Con A (after staining with biotinylated Con A and alkaline phosphatase-conjugated anti-biotin).

Figure 3:
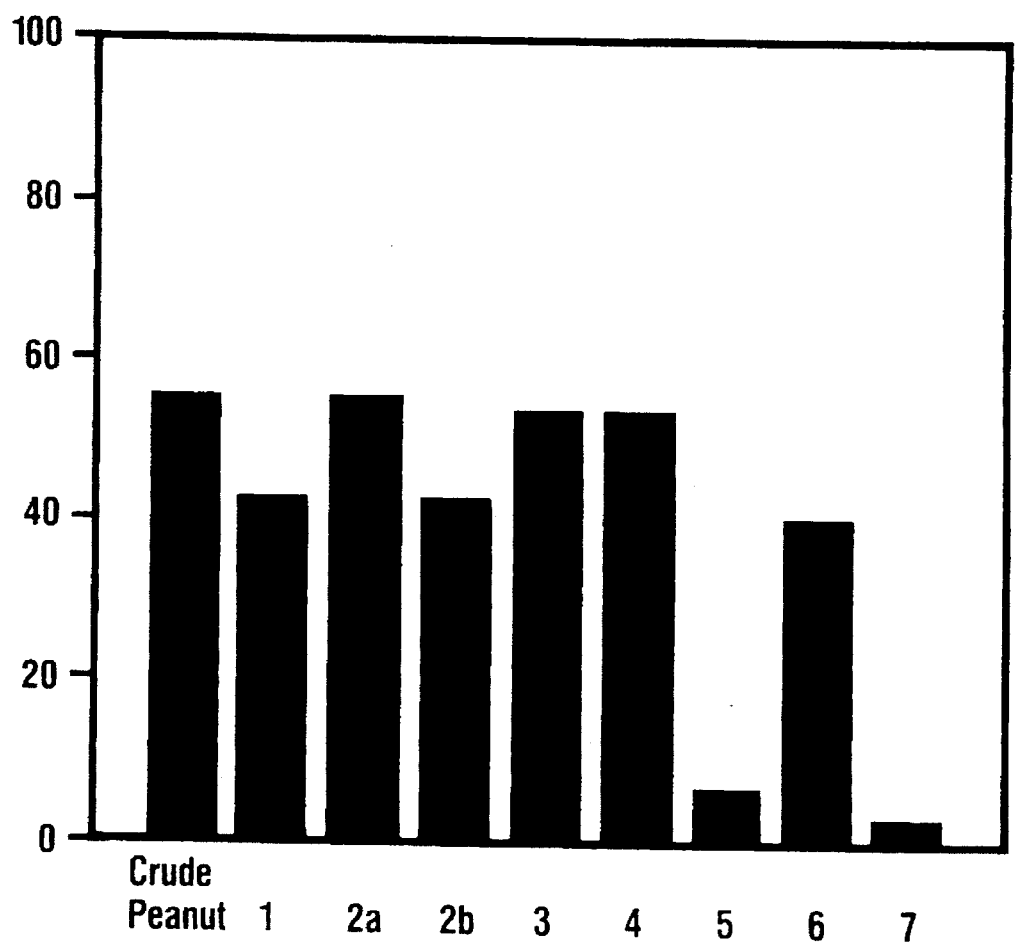
FIG. 3 is a bar graph representation of the amount of antipeanut IgE related to the crude peanut extract and each of the pooled fractions.

ELISA results comparing the crude peanut extract to each isolated fraction are illustrated in FIG. 3. Mono Q 10/10 fractions 2a, 3, and 4 had significant amounts (>50 ng/ml) of binding compared to the crude peanut extract. We additionally tested the serum of six patients (members of the pooled serum) to determine the relative IgE binding to both the crude and the enriched allergen fraction containing the 63.5 kD component (fraction 3). The results are presented in Table 6. Each patient's serum had measurable amounts of peanut-specific IgE to both the crude extract and the 63.5 kD fraction. Serum from patients with AD, elevated serum IgE values, and positive DBPCFCs to milk (patient No. 7) and from healthy normal controls (patient No. 8) did not have detectable peanut-specific IgE to this allergen.

Figure 4:
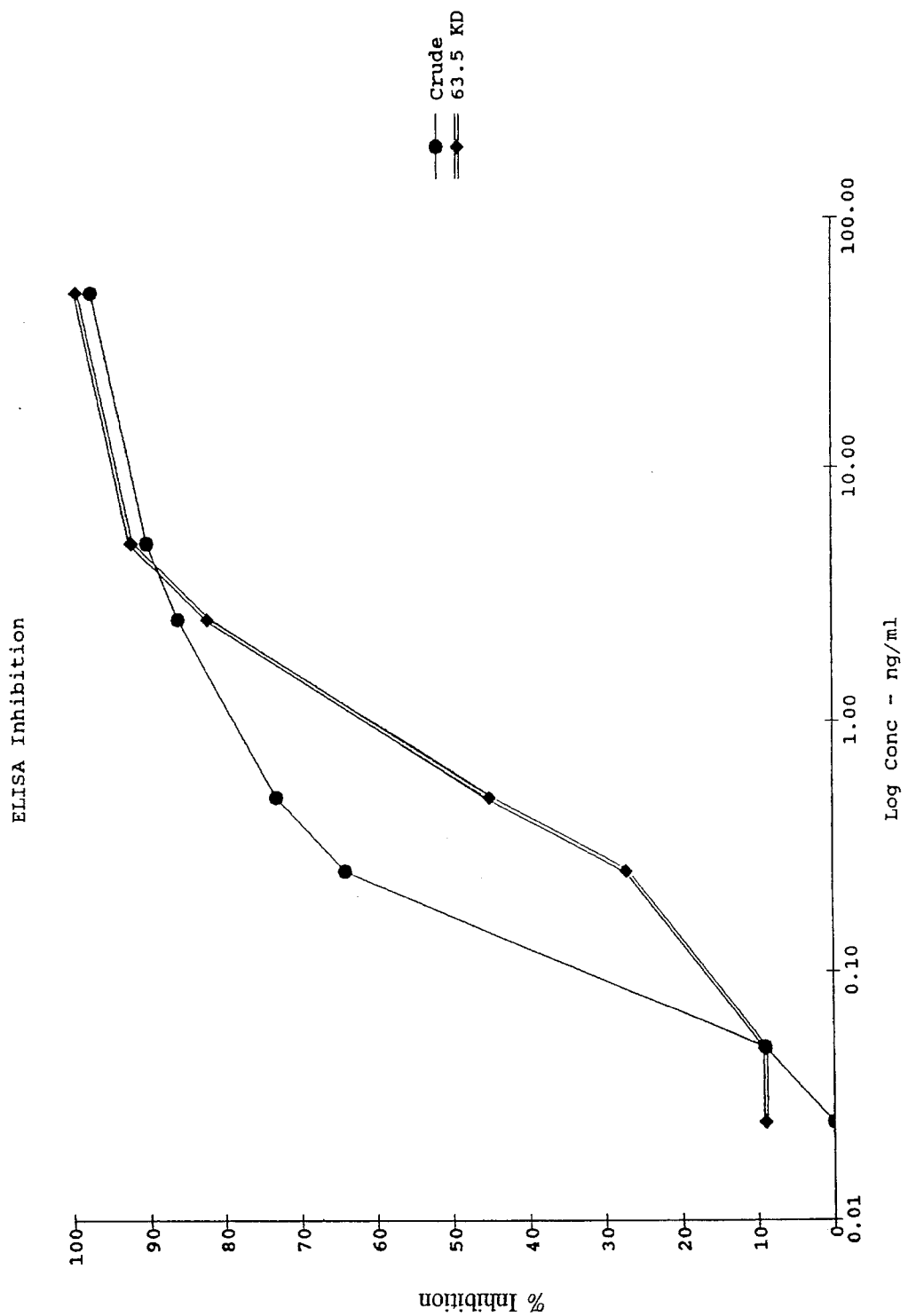
FIG. 4 is a graphical illustration of inhibition relative to concentration of crude peanut extract and fraction 3.

The ELISA-inhibition results are illustrated in FIG. 4. The concentration of the 63.5 kD fraction required to produce 50% inhibition was 5.5 ng/ml compared to 1.4 ng/ml of the crude peanut extract. Control experiments with other food proteins did not demonstrate significant inhibition, demonstrating the specificity of the inhibition assay.

Because immunoblotting and ELISAs of the various anion-exchange fractions demonstrated that fraction 3 contained a major allergen, isoelectric focusing (IEF) and immunoblotting were done on this fraction. Two bands were observed in this allergen that migrated closely together at 63.5 kD on SDS-PAGE, stained with Coomassie brilliant blue, and had a mean pI of 4.55. This protein fraction readily binds IgE from the pooled serum.

Monoclonal antibodies (MAbs) specific to the Ara h I peanut allergen were produced as follows. BALB/c mice were given 3 intraperitoneal injections of 25 µg of the 63.5 kD fraction at 2-week intervals. Two weeks after the final injection the sera were screened for IgG antipeanut antibodies using a peanut-specific IgG ELISA. The positive mice were sacrificed and spleen cells from the sacrificed mice were fused with 8-azaguanine resistant P3X63-Ag8.653 mouse myeloma cells using 50% polyethylene glycol.

Hybrids, which were selected on the basis of the IgG binding assay, were cloned by limiting dilution. Positive clones were selectively expanded and injected intraperitoneally into pristane-primed female BALB/c mice. The resulting ascites was purified by a Protein G column on the FPLC system (Pharmacia).

Four MAbs identified as 8D9, 8F10, 2E9, and 7B3 were used in two-site immunometric assays to measure peanut and other legume antigens by solid phase ELISA. To determine the epitope specificity of each MAb, ELISA-inhibition studies were done with the biotinylated MAb. For detection of specific binding of the MAbs to the 63.5 kD allergen, electrophoresis and immunoblotting were done.

Monoclonal antibody 8F10 was used to affinity purify the allergen identified. Monoclonal antibody 8F10 (approximately 300 mg of purified MAb) was coupled to 8 grams of CNBr-activated Sepharose 4B according to the manufacturer's instructions. Two hundred milliliters of crude peanut extract were absorbed over the column at a flow rate of 20 ml/hr. After adsorption, the column was washed with digestion buffer and the bound allergen eluted using 4 mM HCL, pH 3.0. The collected fractions were screened for peanut-specific allergen by the previously described ELISA and assessed for purity by SDS-PAGE.

Four of the MAbs (subtyped as lambda chain IgG1) were used for immunoblotting against the 63.5 kD allergen. In a two-site immunometric assay each MAb was used as the capture antibody and the serum pool, either the peanut positive IgE serum pool or normal serum pool, was used as the second antibody. The results show that each MAb had significant amounts of binding to the crude peanut material, the 63.5 kD peanut allergen (Ara h I), and the 17 kD peanut allergen (Ara h II) but no significant binding to other legumes, including soy, peas, chick peas, green beans, and lima beans (Table 7). The assays using the normal serum pool showed no significant binding.

In the next ELISA the MAbs were again used as the capture antibody with individual serum used as the second antibody (Table 8). Some individual variation occurred among the individual patients, but each patient included in the peanut positive pool had significant amounts of binding while the patients with normal serum had less than 8.0%.

ELISA-inhibition studies were done with seven MAbs to determine the epitope specificity of each. Biotinylated MAb was incubated with differing concentrations of each of the other MAbs (including a MAb for AltI, the primary allergen from Alternaria). The inhibition was graded from 0+ (none) to 4+ (significant) (Table 2). Monoclonal antibodies 8D9 and 8F10 had the least amount of cross-inhibition between the 4 MAbs.

The allergen purified by MAb 8F10 was isolated from Florunner peanut extract by MAb affinity chromatography. The eluted fraction has 2 major bands on SDS-PAGE at a mean MW of 63.5 kD. The radiolabeled IgE immunoblot with the pooled peanut positive serum showed significant IgE binding.

Since over 90% of six patients with documented food hypersensitivity reactions to peanut demonstrate specific-IgE to the Ara h I allergen (63.5 kD fraction), an ELISA assay which would detect this allergen in food products was developed.

A total of thirty hybridoma subclones were identified for screening. The number of subclones was reduced to twenty by ELISA and SDS-PAGE/Western blotting to determine the binding affinity and specificity using whole peanut extracts. From the twenty subclones the following thirteen were frozen in liquid nitrogen for further testing: hybridoma cell lines 2H9, 2G10, 10B3, 2E9, 4HB, 10A3, 6B5, 7D9, 1B6, 7B3, 8F10, 6F9, and 8D9.

Seven cell lines producing high titer immunoglobulins (MAbs) and having a considerable amount of ascites fluid in mice providing for the recovery of a significant amount of immunoglobulin were selected for further testing (8F10, 8D9, 6B5, 7B3, 2E9, 6F9, and 1B6). The MAbs 8F10 and 8D9 were isolated from the hybridoma cell lines 8F10 and 8D9 supernatants and used as the standard two-site ELISA assay. Cell culture supernatants from the five remaining cell lines were tested to determine their specificity and binding Inhibition in the assays. Small quantities of ascites were also tested by ELISA to determine capture and detection MAb pairings.

Based on the above testing, the preferred capture and detection (biotinylated) MAb pairs include 8F10 and 8D9, 7B3 and 1B6, 2E9 and 6B5, and 2E9 and 8D9. In these monoclonal antibody pairs, either antibody can be used as the capture or detection antibody in the two-site monoclonal antibody enzyme-linked immunosorbent assay of the present invention. For example, assays have been developed using the MAb 8F10 as the capture Ab and MAb 8D9 as the detection Ab or with MAb 8D9 as the capture Ab and MAb 8F10 as the detection (biotinylated) Ab. Other possible MAb pairings include MAbs 7B3 and 2E9, 7B3 and 6B5, 7B3 and 6F9, and 2E9 and 6F9. As shown in Table 2, each of the MAbs 8F10, 8D9, 2E9, 7B3, 1B6, 6B5, and 6F9 were tested as the capture and detection antibody in combination with each of the other antibodies.

Table 9 shows the results of site specificity testing for each of seven MAbs with respect to four binding sites (epitopes on the Ara h I peanut allergen. The results relating to specificity for the four sites labeled A, B, C, and D are based on the use of capture and detection MAbs, while the results relating to the three sites labeled X, Y and Z are based on the use of MAbs in combination with peanut positive serum pool IgE antibody. It is not known whether the three sites A, B, and D are the same three sites X, Y and Z.

IgG1 products from hybridoma cell lines produced against Ara h I were used to develop a 2-site monoclonal antibody ELISA. In one example, monoclonal antibody 8D9 was used as the capture antibody, and monoclonal antibody 8F10 was biotinylated to use as the second antibody.

A crude Florunner peanut extract was used as the standard. Five food products with peanuts on the label (including plain M&M's®, which contain peanuts), five food products without peanuts on the labels, three commercial peanut oils and two commercial soybean oils were used as extract source material. The amount of Ara h I in the peanut-labeled products varied from 1.4 µg/ml to 1777 µg/ml. No Ara h I allergen could be detected in peanut oil, soybean oil or in any of the nonpeanut food extracts. The present ELISA for Ara h I is useful for screening food products for this peanut allergen and for correlating the amount of peanut allergen which might cause significant clinical reactions.

With reference to FIGS. 5–9 of the drawings and in accordance with an exemplary embodiment of the present invention, an ELISA for peanut allergen is produced and analyzed as follows. The 8F10 monoclonal antibody is diluted 1:1000 v/v in coating buffer; concentration is approximately 1–5 µg/ml in 0.1M sodium carbonate/sodium bicarbonate buffer, pH 9.2. One hundred microliters is added to each well of a 96-well microtiter plate and incubated overnight at 4° C. (FIG. 5).

The coating buffer with monoclonal antibody 8F10 is thoroughly washed from the wells with phosphate buffer containing 0.05% Tween 20.

Dilutions of a known peanut extract (0.05–50 µg) and the 63.5 kD allergen are prepared to establish a standard curve. Dilutions of the unknown are prepared to determine if they contain the 63.5 kD allergen. One hundred microliters of the known and unknowns are then added to the individual wells and incubated one hour at 37° C. (FIG. 6).

The solutions are washed from the wells. Only the antigens/allergens that have receptors (epitopes) to the specific monoclonal antibody bind to the capture monoclonal antibody 8F10.

A second monoclonal antibody having a different epitope specificity than that of the capture monoclonal antibody is biotinylated and used as the detection antibody. Monoclonal antibody 8D9 is diluted to a concentration of 1 mg/ml in 0.1 M sodium bicarbonate and dialyzed overnight in the same buffer, A 0.1 ml of biotin-X-NHS per ml (Calbiochem) of antibody solution is added and rocked for two hours at room temperature. The coupling reaction is stopped with 0.1 ml of 1 M ammonium chloride per ml of antibody solution and rocked an additional ten minutes at room temperature. The biotinylated 8D9 monoclonal antibody (Biotin-8D9) is then dialyzed against 500 ml of phosphate buffered saline with 0.01% thimersol, pH 7.4, at 4° C. with stirring. The 500 ml buffer is replaced the next day and dialysis is allowed to continue for an additional 4 hours. The biotinylated antibody solution is adjusted to 2% with bovine serum albumin as a stabilizer; aliquoted into 0.5 ml fractions; and stored frozen at −70° C. One hundred microliters of the biotinylated 8D9 antibody is then added to each well and incubated overnight at 4° C. (FIG. 7). The wells are again washed to remove all of the unbound antibody.

One hundred microliters of a 1:1000 dilution of avidin conjugated horseradish peroxidase enzyme (Vector) is then added to each well for 5 minutes at room temperature (FIG. 8). The biotin on the biotinylated monoclonal antibody and the avidin on the enzyme bind at this stage. The unbound conjugate Is washed from the wells.

One hundred microliters of horseradish peroxidase substrate (Citrate buffer, OPD (Sigma), $H_2O_2$; prepared fresh) is added to each well and incubated at room temperature until a color change develops signified by a colorless solution to a brown/orange/yellow color in the wells (approximately 5–10 minutes). The color development is stopped with the addition of 100 µl of 2N HCL (FIG. 9).

The degree of color development is measured spectrophotometrically (OD490; BioRad plate reader) to determine the absorption. A standard curve is calculated by plotting the concentration of the known peanut concentration versus the optical density of the reaction in the individual wells. The concentrations of the unknown can then be calculated from this curve by interpolation from the curve reading the optical density and determining the concentration from algebraic equations (Software program with the BioRad plate reader, FIG. 1).

Other examples of two-site monoclonal antibody enzyme-linked immunosorbent assays in accordance with the present invention include assays using the following MAb pairs: 7B3 and 1B6, 7B3 and 2E9, 7B3 and 6B5, 7B3 and 6F9, 2E9 and 6B5, 2E9 and 6F9, and 2E9 and 8D9. It should be understood that these seven pairs represent fourteen assay examples since each of the MAbs in these pairs can be used as either the capture or detection antibody.

Because each of the above-described monoclonal antibodies is derived from living hybridoma cells which may perish and since the above description provides one skilled in the art the methodology to produce other hybridoma cells and monoclonal antibodies to the Ara h I peanut allergen, the scope of the present invent/on is not limited to the named hybridoma cell lines and monoclonal antibodies derived therefrom.

The two-site monoclonal antibody enzyme-linked immunosorbent assay (ELISA) has many advantages as compared to the conventional radioimmunoassay (RIA). For example, no isotopes or scintillation counters are required, and the readout may be by eye. The tedious cutting up of trays, loading into tubes, and loading and unloading the counter are all avoided. If a quantitative readout is needed (unnecessary for hybridoma screening) automated reading devices are available which will scan 96 wells in a minute or so, compared to 1–2 h for scintillation counting. Finally, the reagents for ELISA are inexpensive and have a long shelf life. Enzyme-conjugated anti-immunoglobulin or protein A are available commercially from many suppliers. The most

IDENTIFICATION OF ARA H II

Identification and purification of allergens is crucial to the understanding of IgE-mediated disease. Immunologic and structural studies with these purified allergens are the next steps in unraveling this process. Several allergens have been identified that stimulate IgE production and cause IgE-mediated disease in humans. In comparison with the body of work done to identify and purify inhaled allergens, significantly less work has been done on the food allergens.[1-3] Because peanuts are a relatively common and often fatal cause of food hypersensitivity reactions we chose to use this model to study IgE-mediated reactions.[4]

Approximately 60% of children with severe atopic dermatitis (AD) have food hypersensitivity reactions.[5,6] The ability to document food hypersensitivity reactions by double-blind, placebo-controlled, food challenges (DBPCFCs) in this group has allowed appropriate scientific work to be done on the identification of the allergens causing disease.

With the sera of patients who had positive DBPCFCs to peanut, we were able to begin the process of identification and purification of the major peanut allergens. In our previous study we identified and purified Ara h I, a protein with a mean molecular weight of 63.5 kD and a mean isoelectric point (pI) of 4.55.[7] Identification of a second major peanut allergen, Ara h II, was accomplished by use of anion-exchange column chromatography, sodium dodecyl sulfate-polyacrylamide gel electrophoresis (SDS-PAGE), enzyme-linked immunosorbent assays (ELISAs), thin-layer isoelectric focusing (TLIEF), two-dimensional gel immuno-electrophoresis, IgE-specific immunoblotting, carbohydrate analysis, amino acid analysis, and sequencing. This protein has a mean molecular weight of 17 kD and a mean pI of 5.2.

Patients Sensitive to Peanuts

Approval for this study was obtained from the Human Use Committee at the University of Arkansas for Medical Sciences. Nine patients (mean age, 4.2 years) with AD and a positive immediate prick skin test to peanut had either a positive DBPCFC or a convincing history of peanut anaphylaxis (the allergic reaction was potentially life threatening, that is with laryngeal edema, severe wheezing, and/or hypotension) (7 patients had positive DBPCFCs). Details of the challenge procedure and interpretation have been previously discussed.[8] Five milliliters of venous blood were drawn from each patient, allowed to clot, and the serum was collected. An equal volume of serum from each donor was mixed to prepare a nine-person peanut-specific IgE antibody pool.

Crude Peanut Extract

Three commercial lots of southeastern runner (*Arachis hypogaea*), medium grade, from the 1979 crop (North Carolina State University) were used in this study. The peanuts were stored in the freezer at −18° C. until roasted. The three lots were combined in equal proportions and blended before defatting. The defatting process (defatted with hexane after roasting for 13 to 16 minutes at 163° to 177° C.) was done in the laboratory of Dr. Clyde Young (North Carolina State University). The powdered crude peanut was extracted per the recommendations of Yunginger and Jones[9] in 1 mol/L NaCl to 20 mmol/L sodium phosphate (pH 7.0) with the addition of 8 mol/L urea for 4 hours at 4° C. The extract was isolated by centrifugation at 20,000 g for 60 minutes at 4° C. The total protein determination was done by the (BCA) method (Bio-Rad Laboratories, Richmond, Calif.).

Chromatography

Analytic and preparative anion-exchange chromatography was performed with the FPLC system (Pharmacia, Piscataway, N.J.). Anion-exchange chromatography used the PL-SAX column (Anion-exchange column, Polymer Laboratories, Amherst, Mass.). The crude peanut extract was dialyzed against 20 mmol/L Tris-bis-propane (pH 7.2) without urea and 40 mg loaded on the PL-SAX column. A stepwise salt gradient of 0 to 1.5 mol/L NaCl was applied. All fractions of each resolved peak were pooled, dialyzed and lyophilized.

Dot blotting was done to determine which fractions from the anion-exchange column chromatogram contained IgE-binding material. Two hundred microliters of each fraction were blotted with the Mini Blot apparatus (Schleicher and Schuell, Keene, N.H.) onto 0.45 μm nitrocellulose membranes (Bio-Rad). After the membranes were dried, the remaining active sites were blocked with 20 ml of blocking solution (0.5% gelatin with 0.001% thimerosal in 500 ml of phosphate-buffered saline [PBS]) for 1 hour. The procedure is then identical to the immunoblotting for IgE.

Electrophoresis and Immunoblotting

The electrophoresis procedure is a modification of Sutton et al.[10,11] SDS-PAGE was carried out with a 12.5% polyacrylamide separating gel and a stacking gel of 3%. Twenty microliters of a 1 mg/ml solution of each fraction was applied to each well. Replicate samples were applied for independent analysis. Electrophoresis was performed for 4 hours at 0.030 A per gel (E-C Apparatus Corp., St. Petersburg, Fla.) for the 14 cm by 12 cm gels, and for 1 hour at 175 V per gel for the 8 cm by 7.5 cm gels (Mini-Protean II system, Bio-Rad Laboratories). To assure proper protein separation and visualization, Coomassie brilliant blue (Sigma Chemical Co., St. Louis, Mo.) stains were done on gels. For detection of carbohydrate staining material, gels were stained with the modified PAS stain according to the method of Kapitany et al.[12]

Proteins were transferred from the separating gel to a nitrocellulose membrane In a transfer buffer (Tris-glycine) with 10% SDS and 40% methanol.[13] The procedure was done in a transblot apparatus (Bio-Rad Laboratories) for 2 hours (0.150 A). An amido black stain (Bio-Rad Laboratories) was done to assure transfer of the protein.

After removal from the transblot apparatus, the nitrocellulose was placed in blocking solution overnight. The nitrocellulose blot was then washed three times with PBS (PBS with 0.05% Tween 20) and Incubated with the pooled peanut-sensitive IgE serum (1:20 dilution) for 2 hours at 4° C. with rocking. After washing again with PBS three times, alkaline phosphatase-conjugated goat antihuman IgE (1:1000 vol/vol of PBS, Bio-Rad Laboratories) was added and incubated at room temperature with rocking for 2 hours. After again washing with PBS three times, the blot was developed with 250 μl of 30 mg nitro blue tetrazolium in 70% dimethylformamide (NBT) (Bio-Rad Laboratories) and 250 μl of 15 mg of 5-bromo-4-chloro-3-indolyl-phosphate in 70% dimethylformamide (BCIP) (Bio-Rad Laboratories)

commonly used enzymes are horseradish peroxidase and alkaline phosphatase. Both are capable of giving good results, providing that no endogenous enzyme is present.

solutions in 25 ml carbonate buffer (0.2 mol/L, pH 9.8) at room temperature for 15 minutes. The reaction was then stopped by decanting the NBT/BCIP solution and Incubating the nitrocellulose for 10 minutes with distilled water. The blot was air-dried for visual analysis.

ELISA for IgE

A biotin-avidin ELISA was developed to quantify IgE antipeanut protein antibodies with modifications from an assay previously published.[14] The upper two rows of a 96-well microtiter plate (Gibco, Santa Clara, Calif.) were coated with 100 μl each of equal amounts (1 μg/ml) of antihuman IgE monoclonal antibodies, 7.12 and 4.15 (kindly provided by Dr. A. Saxon). The remainder of the plate was coated with one of the peanut products at a concentration of 1 μg/ml in coating buffer (0.1 mol/L sodium carbonate-bicarbonate buffer, pH 9.5). The plate was incubated at 37° C. for 1 hour and then was washed five times with rinse buffer (PBS, pH 7.4, containing 0.05% Tween 20; Sigma Chemicals Co.) immediately and between subsequent incubations. The upper two rows used a secondary standard reference to generate a curve for IgE, ranging from 0.05 to 25 ng/ml.

The serum pool and patient serum samples were diluted (1:20 vol/vol) and dispensed in duplicate in the lower portion of the plate. After incubation for 1 hour at 37° C. and washing, biotinylated, affinity-purified goat antihuman IgE (KPL, Gaithersburg, Md.) (1:1000 vol/vol PBS) was added to all wells. Plates were incubated for 1 hour at 37° C., washed, and 100 μl horseradish peroxidase-avidin conjugate (Vector Laboratories, Burlingame, Calif.) added for 30 minutes. After washing, the plates were developed by addition of a buffer containing O-phenylenediamine (Sigma Chemical Co.). The reaction was stopped by the addition of 100 μl 2-N-hydrochloric acid to each well, and absorbance was read at 492 nm (Titertek Multiscan, Flow Laboratories, McLean, Va.). The standard curve was plotted on log-logit scale by means of simple linear regression, and values for the pool and individual patient samples were read from the curve as "nanogram-equivalent units" per milliliter (nanogram per milliliter).[15,16]

ELISA Inhibition

A competitive ELISA inhibition was done with the FPLC fractions. One hundred microliters of pooled serum (1:20) from the patients with positive challenges was incubated with various concentrations of the FPLC protein fractions (0.00005 to 50 ng/ml) for 18 hours. The inhibited pooled serum was then used in the ELISA described above. The percent inhibition was calculated by taking the food-specific IgE value minus the incubated food-specific IgE value divided by the food-specific IgE value. This number is multiplied by 100 to get the percentage of inhibition.

Isoelectric Focusing

The samples were focused with the LKB Multiphor system using LKB PAG plates, pH gradient 3.5 to 9.5 (LKB, Bromma, Sweden). Five microliters of sample (1 mg/ml) was applied, and an electric current of 200 V was applied for 30 minutes and then increased to 900 to 1200 V for 30 minutes. The gel was fixed and stained with Coomassie brilliant blue following the standard protocol (LKB).

Two-dimensional Gel Electrophoresis

The samples were run according to the method of O'Farrell et al.[17] The first dimension is an isoelectric focusing gel in glass tubing. After making the gel mixture the samples are loaded with overlay solution and 0.02 mol/L NaOH. The samples are run at 400 V #or 12 hours and at 800 V for 1 hour. After removing the gel from the tube, the isoelectric focusing gel is equilibrated for 2 hours In SDS sample butter. The second dimension is 14 cm by 12 cm, 12.5% polyacrylamide gel described in the electrophoresis section. The gels were stained with the pooled peanut-positive serum for IgE-specific bands as above. Amino acid analysis, amino acid sequencing, and carbohydrate analysis.

The 17 kD fraction was run on a 10% mini-gel (Bio-Rad Laboratories) In Tris-glycine buffer and stained with Rapid Reversible Stain (Diversified Biotech, Newton Centre, Mass.). The two bands were cut separately from the gel and electroluted in tris-glycine SDS buffer. After lyophilization the bands were sequenced individually. Automated gas-phase sequencing was performed on an Applied Biosystems model 475A sequencing system (Dr. Bill Lewis, University of Wyoming, Laramie, Wyo.). Amino acid analysis was done with a Hitachi (Hitachi Instruments, Inc., Danbury, Conn.) HPLC L5000 LC controller with a C18 reverse-phase column.

The electroluted 17 kD fraction was analyzed for carbohydrate analysis (Dr. Russell Carlson, Complex Carbohydrate Research Center, University of Georgia, Athens, Ga.). Glycosyl composition analysis on these samples was performed by the preparation and analysis of trimethylsiyl methylglycosides.

RESULTS

Chromotography

Figure 10:
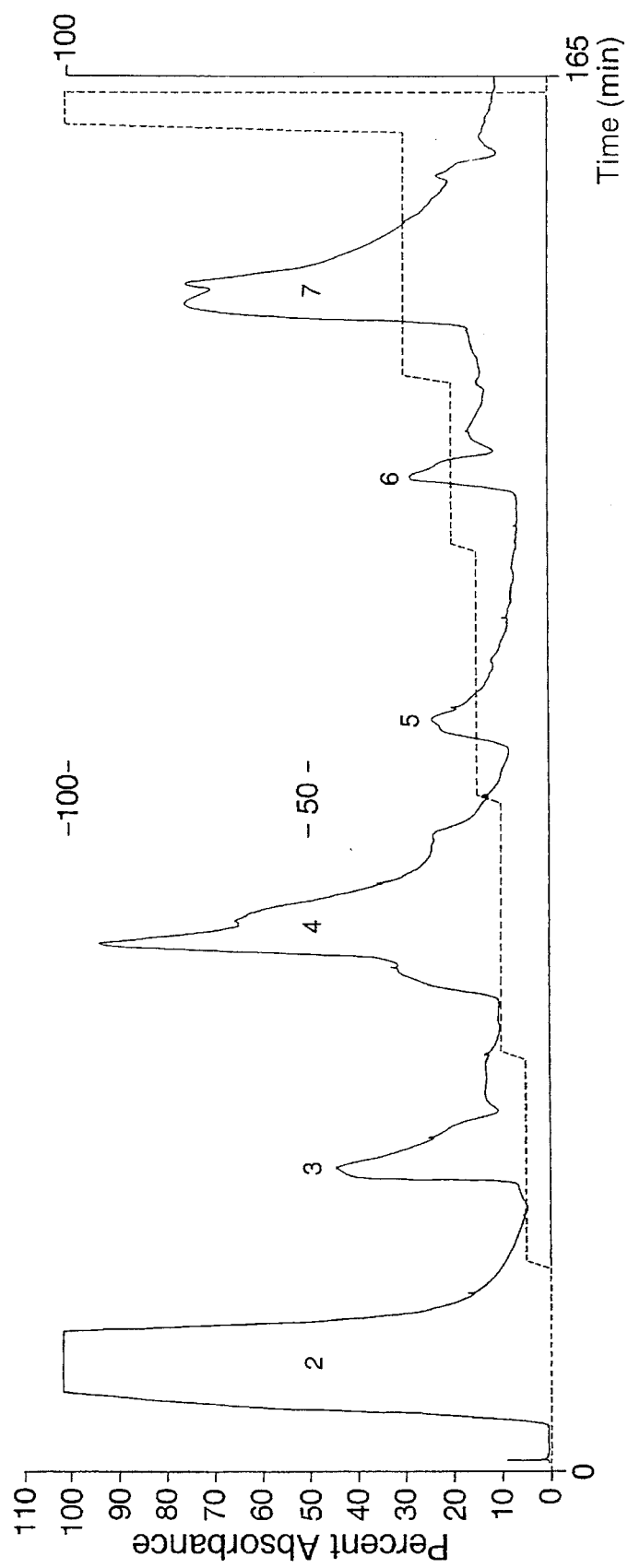
FIG. 10 is a graphical representation of absorbance relative to time.
Figure 11:
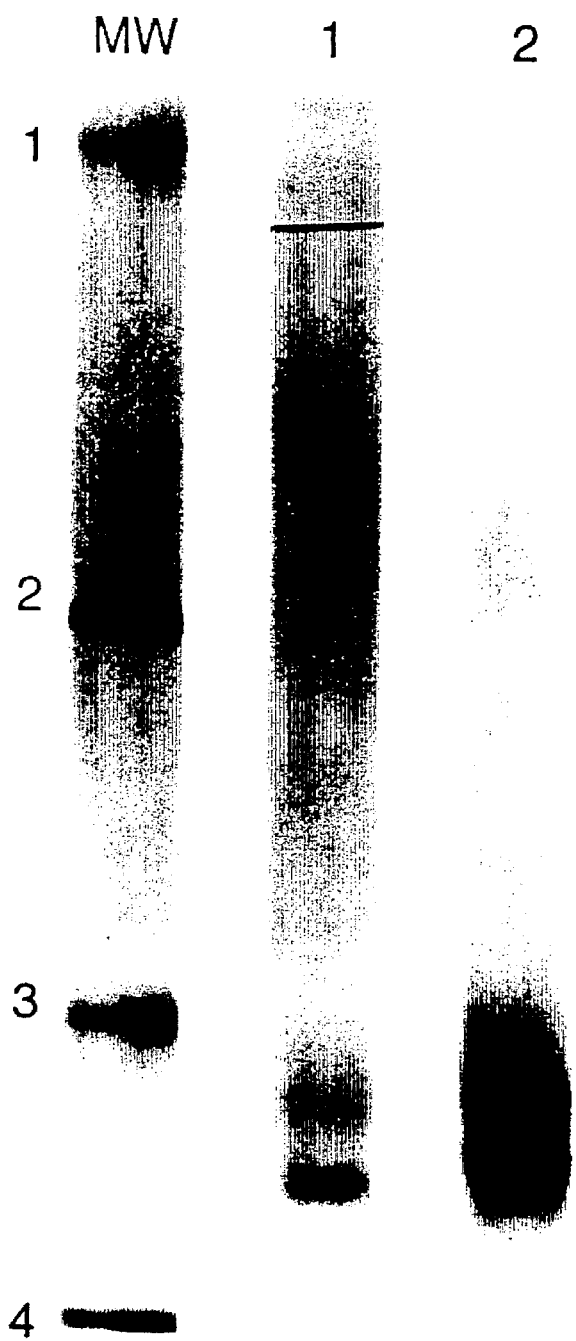
FIG. 11 is an illustration of SDS-PAGE and immunoblotting of the defatted crude peanut extract.

Pilot experiments were conducted with the analytical Mono Q 5/5 (Pharmacia) anion-exchange column to determine the optimal buffer system and salt gradient. Screening for IgE-specific peanut binding components was done by dot blotting of these factions. Scale up and optimization was completed with the PL-SAX column (anion-exchange), with a stepwise salt gradient (0 to 1.5 mol/L NaCl). This procedure separated the crude peanut extract into seven major peaks (FIG. 10). Preliminary dot blotting from this separation identified IgE-binding material in each peak (picture not shown). Multiple runs of this fractionation procedure were performed, and each isolated peak was pooled, dialyzed against 100 mmol/L $NH_4HCO_3$, and lyophilized.

Electrophoresis and Immunoblotting

Initial SDS-PAGE and immunoblotting of the crude peanut extract revealed multiple fractions with several IgE-staining bands.[7] Aliquots of the seven lyophilized fractions from the anion-exchange column were analyzed by SDS-PAGE (date not shown). Each fraction showed 2 to 5 Coomassie brilliant blue staining protein bands. Immunoblotting for specific IgE with the pooled serum revealed IgE-staining bands in each fraction. Fraction 4 showed two large, closely migrating, IgE-specific bands with a mean molecular weight of 17 kD (FIE. 1) (6% by weight of crude peanut extract).

ELISA and ELISA Inhibition

Figure 12:
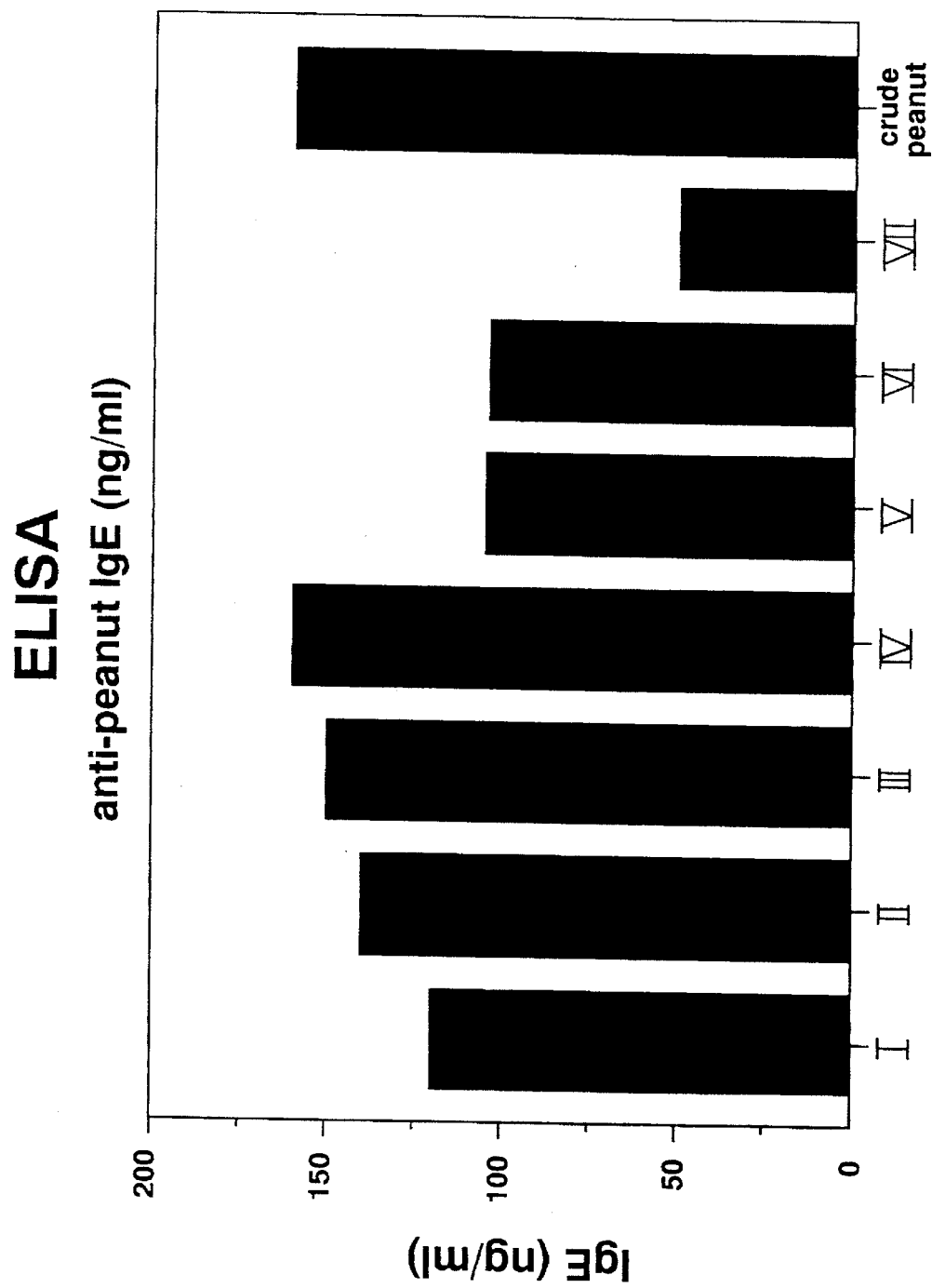
FIG. 12 is a bar graph representation of the amount of antipeanut IgE related to defatted crude peanut extract and pooled fractions.

ELISA results comparing the crude peanut extract with each isolated fraction are shown in FIG. 12. Fractions 1 through 7 all had IgE-binding from the peanut-positive serum pool. We tested individually the serum of six patients (members of pooled serum) to determine the relative IgE-binding material to both the crude peanut, fraction 4 (which contained the 17 kD component), and Ara h I (major component, 63.5 kD fraction). Each patient's serum had measurable amounts of peanut-specific IgE to each. Three of the patients had more peanut-specific IgE (nanogram/milliliter) to the 17 kD fraction than to the 63.5 kD fraction (Table 10).

Figure 13:
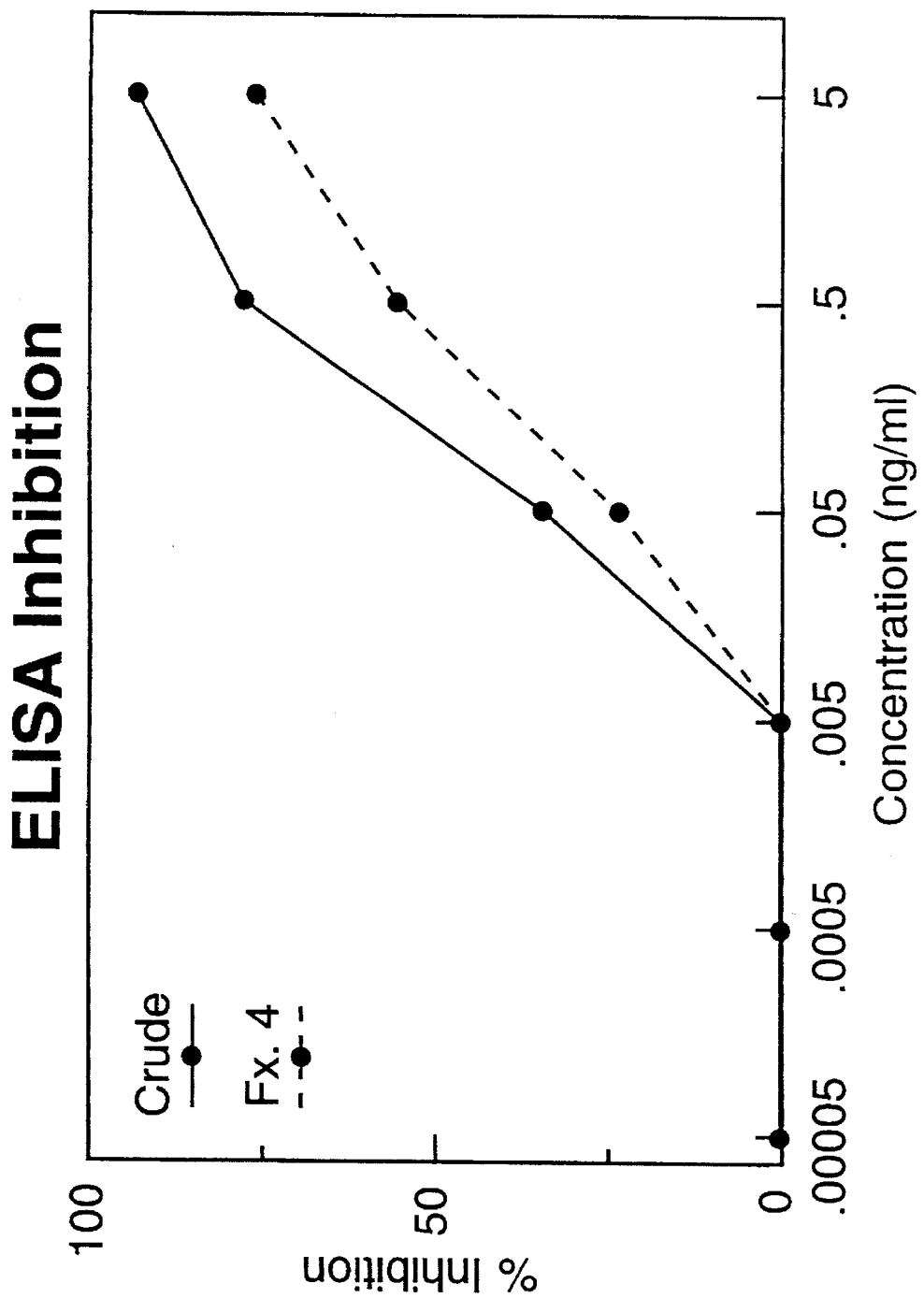
FIG. 13 is a graphical illustration of inhibition relative to concentration of crude peanut extract and anion-exchange fraction 4.

The ELISA inhibition results are shown in FIG. 13. The concentration of the 17 kD fraction required to produce 50% inhibition was 0.4 ng/ml compared with 0.1 ng/ml of the crude peanut extract.[18]

Two-dimensional Gel Electrophoresis

Figure 14:
FIG. 14 is a representation of blue stain of 2-dimensional gel with fraction 4 containing the 17 kD allergen.

Because immunoblotting and ELISAs of the various anion-exchange fractions suggested that fraction 4 appeared to contain a major allergen, isoelectric focusing was done on this fraction. The two bands in this allergen, which migrated closely together at a mean molecular weight of 17 kD on SDS-PAGE stained with Coomassie brilliant blue, had a pI of 5.2 (gel not shown). FIG. 14 shows the Coomassie-stained gel of the 17 kD fraction. One can see the protein divided into four distinct areas at a mean molecular weight of 17 kD and a mean pI of 5.2. Amine acid analysis, amine acid sequencing, and carbohydrate analysis Table 11 shows the complete amine acid analysis of the purified peanut fraction. The fraction was particularly rich in glutamic acid, aspartic acid, glycine, and arginine.

The amine acid sequence for both 17 kD bands is shown in Table 12. The upper band is identified as SEQ ID NO:1 and the lower band is identified as SEQ ID NO:2. The sequence for the second 17 kD band was essentially identical. Sequencing data from the N-terminus of the lower band revealed the following initial 9 amino acids: (*)-Q-Q-(*)-E-L-Q-D-L (SEQ ID NO:3). Molecular weight discrepancies may be a result of carbohydrate composition in the two isoallergens. There are no known similar N-terminal sequences found in PIR, GEN-BANK, or SWISS-PROTEIN.

The 17 kD fraction was found to be 20% carbohydrate with significant levels of galacuronic acid, arabinose, and xylose (Table 13).

DISCUSSION

Individuals are genetically prone to produce IgE to specific antigens and to have allergic disease. No known features have been found to distinguish allergens as unique antigens.[19] The route of allergen administration, the dosage, the frequency of exposure, and genetic factors all determine the type and severity of the individual's allergic response. Three seemingly distinct foods account for approximately 80% of positive food challenges In children.[5-7] It is apparent that in addition to the fact that these foods are consumed frequently in the diet of children, other factors in either the allergen (food) itself or in the processing of these allergens cause these foods to be responsible for most food hypersensitivity reactions.

Most allergens are low molecular weight proteins or glycoproteins (5 to 50 kD).[20] Recent knowledge about the amino acid sequence of known allergens has not revealed any special features that would be associated with IgE antibody formation.[19] To first identify and then purify the allergens is crucial to a better understanding of the allergic response. Various biochemical techniques have been used to purify allergens from pollen, mite, and animal dander. These techniques include gel filtration, anion-exchange chromotography, and isoelectric focusing.[19] Recent advances in chromatography, including the FPLC (Pharmacia) and immunoaffinity columns with monoclonal antibodies specific for the purified allergens, has allowed easier and faster identification and purification of allergens.

House dust mite, ragweed, and venom allergens are among those allergens that have been isolated and well characterized. Food allergens have been less studied. The food allergens that have been Identified and characterized include Gad c I (cod), Gal d II (ovalbumin), and antigen I (shrimp).[1,2]

Because of the prevalence and severity of adverse reactions to peanuts, several previous studies have examined the possibly relevant peanut allergens.[21-27] Multiple molecular weight peanut proteins have been Identified from these various studies. Meier-Davis et al.[24] Identified three major allergenic fractions, one of which had a molecular weight of 15 kD, which is close to the molecular weight of the allergen Ara h II we have identified. No further identification or characterization of this protein is available.

In a previous study we Identified Ara h I, a 63.5 kD allergen from peanuts with a pI of 4.55.[7] This allergen was similarly purified and identified with a combination of anion-exchange chromatography, SDS-PAGE, ELISA, TLIEF, and ELISA inhibition. The allergen described In this report has two major bands, with an apparent mean molecular weight of 17 kD on SDS-PAGE and a mean pI of 5.2. This fraction bound specific antipeanut IgE from the peanut-positive pool In the ELISA and In the immunoblotting experiments. When used in the ELISA-inhibition studies, the 17 kD fraction significantly Inhibited the IgE binding from the peanut-positive pool. In preliminary studies we have used the 17 kD allergen to inhibit binding from the pooled peanut-positive IgE serum to our previously described Ara h I. There does appear to be a moderate amount of inhibition of IgE binding to Ara h I produced by the 17 kD allergen. Amino acid sequencing of Ara h I will help to resolve the identity of similar epitopes for IgE between the unique allergens.

According to recent recommendations by a recent international committee (IUIS) for proper identification of allergens we have designated this fraction Ara h II.[20] This fraction has been purified from a crude peanut extract from Florunner peanuts (*Arachis hypogaea*) by anion-exchange chromatography. The fraction was identified as a major allergen by SDS-PAGE, ELISA, ELISA inhibition, TLIEF, amino acid analysis and sequencing, carbohydrate analysis, and two-dimensional gels.

As we have previously speculated, Ara h II is likely to be the second of several major and minor allergens isolated from peanuts. The identification of the allergenic components in foods will allow new studies to elucidate more comprehensively the body's immune response to these allergens. Future work in this area will be directed toward molecular identification and characterization of both B- and T-cell epitopes.

In accordance with the present invention, isolated and purified peanut allergen Ara h II is used as an antigen to produce monoclonal antibodies having a specificity for the Ara h II allergen and to develop a monoclonal antibody enzyme linked immunosorbent assay for the peanut allergen Ara h II using the same methods and procedures as described above with respect to the development of monoclonal antibodies and assays for the peanut allergen Ara h I. In accordance with one example of the present invention, a method for detecting the presence and quantity of the peanut allergen Ara h II in a sample using a two-site monoclonal antibody enzyme linked immunosorbent assay includes the steps of: coating an assay test surface with a layer of capture monoclonal antibodies having a specificity for the Ara h II allergen, incubating the coated test surface to allow the capture monoclonal antibodies to adhere to the test surface, washing the coated test surface to remove any unadhered capture monoclonal antibodies, adding a sample to the coated test surface, incubating the coated test surface to allow the adhered capture monoclonal antibodies to capture any Ara h II peanut allergen present in the sample, washing the coated test surface to remove the uncaptured peanut allergen and remaining sample, adding a layer of biotinylated monoclonal antibodies having a specificity for the Ara h II allergen to the coated test surface, incubating the coated test surface to allow the biotinylated monoclonal antibodies to bind to the captured peanut allergen, washing the coated test surface to remove unbound biotinylated monoclonal antibodies, adding horseradish peroxidase-avidin conjugate to the coated test surface, allowing the horseradish-peroxidase, avidin conjugate to bind to the biotinylated monoclonal antibodies, washing the coated test surface to remove any unbound horseradish peroxidase-avidin conjugate, adding citric acid substrate to the coated test surface to develop a color change indicative of the quantity of bound horseradish peroxidase, adding a stopping agent to stop the development of the color change, and reading the assay to determine the presence and/or quantity of the peanut allergen Ara h II. Also, in accordance with a more particular method, the capture monoclonal antibodies and biotinylated monoclonal antibodies demonstrate specificity for different binding sites on the peanut allergen Ara h II.

Moreover, in accordance with another embodiment of the present invention, test kits for detecting and quantifying the peanut allergens Ara h I and Ara h II include an ELISA test tray, the capture and biotinylated monoclonal antibodies, allergen standards, and the necessary reagents for practicing the described assay method.

Thus, it will be appreciated that as a result of the present invention, two major peanut allergens have been isolated and a highly effective two-site monoclonal antibody enzyme-linked immunosorbent assay and method is provided by which the principal objective, among others, is completely fulfilled. It is contemplated, and will be apparent to those skilled in the art from the preceding description and accompanying drawings, that modifications and/or changes may be made in the illustrated embodiments without departure from the present invention. Accordingly, it is expressly intended that the foregoing description and accompanying drawings are illustrative of preferred embodiments only, not limiting, and that the true spirit and scope of the present invention be determined by reference to the appended claims.

| LIST OF ABBREVIATIONS | |
|---|---|
| DBPCFC: | Double-blind, placebo-controlled, food challenge |
| SDS: | Sodium dodecyl sulfate |
| PAGE: | Polyacrylamide gel electrophoresis |
| NBT: | 30 mg nitro blue tetrazolium in 70% dimethylformamide |
| BCIP: | 15 mg of 5-bromo-4-chloro-3-indolyl-phosphate in 70% dimethylformamide |
| TLIEF: | Thin-layer isoelectric focusing |
| ELISA: | Enzyme-linked immunosorbent assay |
| AD: | Atopic dermatitis |
| pI: | Isoelectric point |
| CRIB: | Crossed radioiamunoelectrophoresis |
| Ab: | Antibody |
| IUIS: | International Union of Immunological Societies |
| FPLC: | Fast protein liquid chromatography |
| PAS: | Periodic acid-Schiff |
| MAb: | Monoclonal antibody |
| IEF: | Isoelectric focusing |
| Con A: | Concanavalin A |
| PBS: | Phosphate-buffered saline |
| RIA: | Radioimmunoassay |

LIST OF REFERENCES

1. Anderson J A, Sogn D D, eds. Adverse reactions to foods. Hyattsvlle, Md.: 1984; *NIH publication no.* 84-2442:7–26.

2. Metcalfe D D. Food allergens. Clin Rev Allergy 1985;3:331–49.

3. Lemanske RF, Taylor SL. Standardized extracts, foods. *Clin Rev Allergy* 1987;5:23–36.

4. Sampson H A. Peanut anaphylaxis. *J ALLERGY CLIN IMMUNOL* 1990;86:1–3.

5. Sampson H A. Role of immediate food hypersensitivity in the pathogenesis of atopic dermatitis. *J ALLERGY CLIN IMMUNOL* 1983;71:473–80.

6. Sampson H A, McCaskill C C. Food hypersensitivity in atopic dermatitis: evaluation of 113 patients. *J Pediatr* 1095; 107:669–75.

7. Burks A W, Williams L W, Helm R M, Connaughton C, Cocktell G, O'Brien T. Identification of a major peanut allergen, Ara h I, in patients with atopic dermatitis and positive peanut challenges. *J ALLERGY CLIN IMMUNOL* 1991;88:172–9.

8. Burks A W, Mallory S B, Williams L W, Shirrell H A. Atopic dermatitis: clinical relevance of food hypersensitivity reactions. *J Pediatr* 1988;113:447–51.

9. Yunginger J W, Jones R T. A review of peanut chemistry; implications for the standardization of peanut extracts. *In: Proceedings of the Fourth International Paul Ehrlich Seminar on the Regulatory Control and Standardization of Allergenic Extracts.* Bethesda, Md.: Oct. 16–17, 1985. Stuttgart: Gustav Fischer Verlag, 1987:251–64.

10. Laemmli UK. Cleavage of structural proteins during the assembly of the head of bacteriophage T4. *Nature* 1970;227:680–5.

11. Sutton R, Wrigley C W, Baldo B A, Detection of IgE and IgG binding proteins after electrophoresis transfer from polyacrylamide gels. *J Immunol Methods* 1982;52:183–6.

12. Kapitany R, Zebrowski E J. A high resolution PAS strain for polyacrylamide gel electrophoresis. *Anal Biochem* 1973; 65:361–9.

13. Towbin H, Staehelin T, Gordan J. Electrophoretic transfer of proteins from polyacrylamide gels to nitrocellulose sheets: procedure and some applications. *Proc Natl Acad Sci USA* 1979;76:4350–4.

14. Burks A W, Sampson H A, Buckley R H. Anaphylactic reactions following gammaglobulin administration in patients with hypogammaglobulinemia: detection of IgE antibodies to IgA. *N Engl J Med* 1986;314:560–4.

15. Burks A W, Brooks J R, Sampson H A. Allergenicity of major component proteins of soybean determined by enzyme-linked immunosorbent assay (ELISA) and immunoblotting in children with atopic dermatitis and positive soy challenges. *J ALLERGY CLIN IMMUNOL* 1988;81:1135–42.

16. Burks A W, Williams L W, Casteel H B, Fiedorek S C, Connaughton C A. Antibody response to milk proteins in patients with milk-protein intolerance documented by challenge. *J ALLERGY CLIN IMMUNOL* 1990;85:921–7.

17. O'Farrell P H. High resolution two-dimensional electrophoresis of proteins. *J Biol Chem* 1975;250:4007–21.

18. Jusko J W. Corticosteroid pharmacodynamics: models for a broad array of receptor-mediated pharmacologic effects. *J Clin Pharmacol* 1990;30:303–10.

19. Marsh D G. Allergens and the genetics of allergy. In: Sela M, ed. The antigens. New York: Academic Press, 1975:271–359.

20. Chapman M D. Purification of allergens. *Curr Opin Immunol* 1989;1:647–53.

21. Nordlee J A, Taylor S L, Jones R T, Yunginger J R. Allergenicity of various peanut products as determined by RAST inhibition. *J ALLERGY CLIN IMMUNOL* 1981;68:376–82.

22. Heiner D C, Neucere N J. RAST analyses of peanut allergens [Abstract]. *J ALLERGY CLIN IMMUNOL* 1975;55:82.

23. Barnett D, Baldo B A, Howden MEH. Multiplicity of allergens In peanuts. *J ALLERGY CLIN IMMUNOL* 1983;72:61–8.

24. Meier-Davis S, Taylor S L, Nordlee J, Bush R. Identification of peanut allergens by immunoblotting [Abstracts]. *J ALLERGY CLIN IMMUNOL* 1987;79:218.

25. Barnett D, Howden M E H, Bonham B, Burley R W. Aspects of legume allergy research. *Proc Sydney Allergy Group* 1985;4:104–18.

26. Taylor S L, Nordlee J A, Yunginger J W, Jones R T, Sach M I, Bush R K. Evidence for the existence of multiple allergens in peanuts [Abstract]. *J ALLERGY CLIN IMMUNOL* 1982;69:128.

27. Sachs M I, Jones R T, Yunginger R W. Isolation and partial characterization of a major peanut allergen. *J ALLERGY CLIN IMMUNOL* 1981;67:27–34.

TABLE 1

Individual IgE-antibody to peanut allergens (ng/ml)

| Pt | Crude peanut | Ara h II | Ara h I |
|---|---|---|---|
| #1 | 4.2 | 21.0 | 14.6 |
| #2 | 7.0 | 11.4 | 13.0 |
| #3 | 285.2 | 285.8 | 380.0 |
| #4 | 1.0 | 2.0 | 3.2 |
| #5 | 11.4 | 19.4 | 17.0 |
| #6 | 5.8 | 12.0 | 9.8 |
| Normals (×2) | <0.05 | <0.05 | <0.05 |

TABLE 2

ELLISA inhibition for 7 monoclonal antibodies to Ara h I

| Biotinylated monoclonal | Inhibiting antibody | | | | | | | |
|---|---|---|---|---|---|---|---|---|
| | 8F10 | 8D9 | 2E9 | 7B3 | 1B6 | 6B5 | 6F9 | Alt 1 |
| 8F10 | 71% | 10% | 11% | 11% | 2% | 5% | 5% | 0% |
| 8D9 | 31% | 82% | 34% | 0% | 28% | 26% | 5% | 0% |
| 2E9 | 26% | 35% | 53% | 15% | 29% | 27% | 10% | 0% |
| 7B3 | 22% | 4% | 0% | 50% | 16% | 13% | 10% | 0% |
| 1B6 | 0% | 43% | 39% | 0% | 55% | 34% | 6% | 0% |
| 6B5 | 22% | 52% | 35% | 18% | 52% | 75% | 8% | 0% |
| 6F9 | 20% | 20% | 12% | 12% | 35% | 27% | 54% | 0% |

TABLE 3

SAMPLES

| Peanut | Others | Oils |
|---|---|---|
| Plain M & M | Twix | Olive |
| Peanut M & M | Skor | Garlic |
| Whatchamacalit | Nestle Crunch | Vegetable |
| Snickers | 3 Musketeers | Canola |
| Peanut Butter M & M | Kit Kat | Corn |
| | | Peanut |

TABLE 4

63.5 kD Two-site Immunometric Assay (Candy)

| Peanut | (ng/ml) | Others | (ng/ml) |
|---|---|---|---|
| Plain M & M | 7.35 | Twix | 0 |
| Snickers | 219.00 | Skor | 0 |
| Peanut M & M | 221.00 | Nestle Crunch | 0 |
| Whatchamacalit | 233.00 | 3 Musketeers | 0 |
| Peanut Butter M & M | 299.00 | Kit Kat | 0 |

TABLE 5

63.5 kD Two-site immunometric Assay

| Oils | (ng/ml) |
|---|---|
| Olive | 0 |
| Garlic | 0 |
| Vegetable | 0 |
| Canola | 0 |
| Corn | 0 |
| Peanut | 0 |

TABLE 6

Individual IgE Ab to peanut allergens (nanograms per milliliter)

| Patient | Crude peanut | 63.5 kd |
|---|---|---|
| 1 | 4.21 | 4.6 |
| 2 | 7.0 | 13.0 |
| 3 | 285.2 | 380.0 |
| 4 | 1.0 | 3.2 |
| 5 | 11.4 | 17.0 |
| 6 | 5.8 | 9.8 |
| 7 | ND | ND |
| 8 | ND | ND |

TABLE 7

ELISA - IgE (pooled peanut positive serum)

| PROTEIN | CAPTURE ANTIBODY | | | |
|---|---|---|---|---|
| | 8D9 | 8F10 | 2E9 | 7B3 |
| Peanut Positive IgE Serum Pool | | | | |
| 63.5 kD fraction | 4+ | 4+ | 4+ | 4+ |
| crude peanut | 4+ | 4+ | 4+ | 4+ |
| 17 kD fraction | 2+ | 2+ | 2+ | 2+ |
| soy | 0+ | 0+ | 0+ | 0+ |
| peas | 1+ | 1+ | 1+ | 1+ |
| chick peas | 1+ | 1+ | 1+ | 1+ |
| green beans | 0+ | 0+ | 0+ | 0+ |
| lima beans | 0+ | 0+ | 0+ | 0+ |
| ovalbumin | 0+ | 0+ | 0+ | 0+ |
| Normal serum pool | | | | |
| crude peanut | 0+ | 0+ | 0+ | 0+ |
| 63.5 kD fraction | 0+ | 0+ | 0+ | 0+ |

Table 7. We examined various proteins in the two-site immunometric assay with the mAb as the capture antibody and the peanut positive IgE serum pool as the second antibody. Table 7 shows the results of this assay. The binding was graded from 0+ (none) to 4+ (significant).

TABLE 8

IgE (individual peanut positive serum)

| PATIENTS | CAPTURE ANTIBODY | | | |
|---|---|---|---|---|
| | 8D9 | 8F10 | 2E9 | 7B3 |
| #1 | 38% | 28.3% | 35.3% | 32.3% |
| #2 | 227.8% | 156% | 282.2% | 164.3% |
| #3 | 61.6% | 82.9% | 38.7% | 27.4% |
| #4 | 18.2% | 14.4% | 13.6% | 13.1% |
| #5 | 21.2% | 24.8% | 38% | 23.1% |
| #6 | 57.8% | 71.9% | 56% | 64.8% |
| Peanut positive pool | 165% | 144% | 125.7% | 143% |
| #7 | 7.1% | 7.4% | 0.0% | 0.0% |
| #8 | 7.1% | 1.8% | 4.5% | 3.5% |

Table 8. Table 8 shows the results of individual peanut positive patients in a similar two-site assay. Patients with normal serum IgE (#7) or patients (#8) with elevated serum IgE but who were not challenge positive to peanut.

TABLE 9

Site specificity of Ara h I monoclonal antibodies

| (a) | A | B | C | D |
|---|---|---|---|---|
| | 8F10 | 8D9 | 7B3 | 6F9 |
| | | 2E9 | | |
| | | 1B6 | | |
| | | 7B3 | | |

TABLE 9-continued

Site specificity of Ara h I monoclonal antibodies

| (b) | X | Y | Z |
|---|---|---|---|
| | 8F10 | 8D9 | 6F9 |
| | | 6B5 | |

TABLE 10

Concentrations (ng/ml) of peanut-specific IgE binding to the crude peanut extract, Ara h I (63.5 kd allergen), and fraction 4 (from FPLC) (17 kd allergen)

| Patient | Crude peanut (ng/ml) | Ara h I (ng/ml) | Fraction 4 (ng/ml) |
|---|---|---|---|
| 1 | 4.2 | 21.0 | 14.6 |
| 2 | 7.0 | 11.4 | 13.0 |
| 3 | 285.2 | 285.8 | 380.0 |
| 4 | 1.0 | 2.0 | 3.2 |
| 5 | 11.4 | 19.4 | 17.0 |
| 6 | 5.8 | 12.0 | 9.8 |
| 7 | <0.05 | <0.05 | <0.05 |
| 8 | <0.05 | <0.05 | <0.05 |
| Normals | <0.05 | <0.05 | <0.05 |

Patients 1–6 are patients with AD and positive DBPCFCs to peanut.
Patient 7 is a patient with AD who had positive DBPCFC to milk and elevated serum IgE values but did not have positive skin test results or positive challenge to peanut (n = 2).
Patient 8 is a healthy control patient from the serum bank in the ACH Special Immunology Laboratory (n = 2).

TABLE 11

Amino acid analysis of Ara h II

| Amino acid | Residues/molecule |
|---|---|
| Asp | 12.2 |
| Glu | 24.8 |
| Ser | 9.8 |
| His | 1.3 |
| Gly | 11.3 |
| Thr | 2.2 |
| Arg | 10.8 |
| Ala | 5.4 |
| Tyr | 3.9 |
| Met | 2.7 |
| Val | 2.4 |
| Phe | 2.4 |
| Ile | 2.9 |
| Leu | 7.9 |

TABLE 12

Sequencing of upper band (SEQ ID NO: 1) and lower band (SEQ ID NO: 2) of electroluted 17 kd peanut allergen

| Upper band | * — Gln — Gln — * — Glu — Leu — Gln — * — Asp — * — * — * |
| Lower band | * — Gln — Gln — * — Glu — Leu — Gln — Leu — Gln — Asp — Leu — Glu — * — * |
| Upper Band | — Gln — Ser — Gln — Leu — Glu — Arg — Ala — Asp — Leu — Arg — Pro — (Gly) |
| Lower Band | — Gln — Ser — Gln — Leu — Glu — Asp — Ala — Asn — Leu — Arg — Pro — Arg |
| Upper Band | — Glu — Gln — * — Leu — Met — * — Lys — Ile |
| Lower Band | — Glu — Gln — * — Leu — Met — * — Lys — Ile |

*Unable to identify amino acid.

TABLE 13

Glycosyl composition analysis of 17 kd allergen

| Glycosyl residue | Ara h II (μg/total) |
|---|---|
| Arabinose | 14.0 |
| Rhamose | 2.8 |
| Fucose | 0.58 |
| Xylose | 9.3 |
| Mannose | 2.5 |
| Galactose | 4.4 |
| Glucose | 5.0 |
| Galacuronic acid | 41.0 |
| Galactosamine | ND |

ND, None detected.

What is claimed as invention is:

1. An isolated and purified peanut allergen designated Ara h II and having a mean molecular weight of 17 kD as determined by IgE-specific immunoblotting and a mean isoelectric point of 5.2 as determined by two-dimensional gel electrophoresis.

2. The allergen of claim 1 have an initial nine amino acid N-terminus sequence of (*)-Q-Q-(*)-E-L-Q-D-L (SEQ ID NO:3).

3. The allergen of claim 1 with an amino acid N-terminus sequence having SEQ ID NO:1.

4. The allergen of claim 1 with an amino acid N-terminus sequence having SEQ ID NO:2.

5. The allergen of claim 1 having at least one of the amino acid N-terminus sequences of SEQ ID NO:1 and SEQ ID NO:2.

* * * * *